(12) United States Patent
Scheiner et al.

(10) Patent No.: US 11,601,587 B2
(45) Date of Patent: Mar. 7, 2023

(54) SYSTEM AND METHOD FOR MONITORING PLANTS IN PLANT GROWING AREAS

(71) Applicant: VIEWNETIC LTD., Tel Aviv (IL)

(72) Inventors: David Scheiner, Savyion (IL); Eilat Tal, D.N. Arava (IL); Hai Benron, Haifa (IL)

(73) Assignee: VIEWNETIC LTD., Tel Aviv (IL)

( * ) Notice: Subject to any disclaimer, the term of this patent is extended or adjusted under 35 U.S.C. 154(b) by 0 days.

(21) Appl. No.: 17/274,576

(22) PCT Filed: Sep. 9, 2019

(86) PCT No.: PCT/IL2019/051007
§ 371 (c)(1),
(2) Date: Mar. 9, 2021

(87) PCT Pub. No.: WO2020/049576
PCT Pub. Date: Mar. 12, 2020

(65) Prior Publication Data
US 2022/0053122 A1    Feb. 17, 2022

Related U.S. Application Data

(60) Provisional application No. 62/728,815, filed on Sep. 9, 2018.

(51) Int. Cl.
*H04N 5/232* (2006.01)
*A01M 7/00* (2006.01)
(Continued)

(52) U.S. Cl.
CPC .......... *H04N 5/23218* (2018.08); *A01G 7/00* (2013.01); *A01M 7/0089* (2013.01);
(Continued)

(58) Field of Classification Search
CPC .......... H04N 5/23218; H04N 5/23299; H04N 5/2354; H04N 5/247; H04N 7/188;
(Continued)

(56) References Cited

U.S. PATENT DOCUMENTS 11,074,447 B1 * 7/2021 Fox ................. G08G 5/0069
2007/0153114 A1   7/2007 Ueda et al.
(Continued)

FOREIGN PATENT DOCUMENTS

EP        3171327 A1    6/2015
WO     2014/106814 A2   7/2014
(Continued)

OTHER PUBLICATIONS

Jacobs, David E. et al: "Focal Stack Compositing for Depth of Field Control", Jan. 31, 2012.
(Continued)

*Primary Examiner* — Nasim N Nirjhar
(74) *Attorney, Agent, or Firm* — Browdy and Neimark, P.L.L.C.

(57) ABSTRACT

A monitoring system is presented for monitoring plants' conditions in one or more plant growing areas. The system comprises: a data collection system configured and operable to provide characterization data about plants in said one or more plant growing areas, the data collection system comprising data collection modules of at least first and second different types, the first type data collection module comprising a first imaging device of predetermined first optical properties and the second type data collection module comprising a second imaging device of predetermined second optical properties different from the first optical properties, the characterization data provided by at least one of the first and second imaging devices being indicative of various parameters of the plants being imaged; and a control system
(Continued)

configured and operable to be in data communication with an analyzer to be responsive to operational data received from the analyzer and being based on analysis of the image data indicative of one or more plants being imaged by the first type imaging device, to selectively activate the second type imaging device to apply the second type imaging to at least a part of said one or more plants.

24 Claims, 12 Drawing Sheets

(51) Int. Cl.
| | | |
|---|---|---|
| *B64C 39/02* | (2006.01) | |
| *G01B 11/24* | (2006.01) | |
| *G01N 21/31* | (2006.01) | |
| *G01N 21/84* | (2006.01) | |
| *G01N 33/00* | (2006.01) | |
| *H04N 5/247* | (2006.01) | |
| *A01G 7/00* | (2006.01) | |
| *H04N 5/235* | (2006.01) | |
| *H04N 7/18* | (2006.01) | |

(52) U.S. Cl.
CPC ............ *B64C 39/024* (2013.01); *G01B 11/24* (2013.01); *G01N 21/31* (2013.01); *G01N 21/84* (2013.01); *G01N 33/0098* (2013.01); *H04N 5/2354* (2013.01); *H04N 5/23299* (2018.08); *H04N 5/247* (2013.01); *H04N 7/188* (2013.01); *B64C 2201/123* (2013.01); *G01N 2021/8466* (2013.01)

(58) Field of Classification Search
CPC ......... A01G 7/00; A01G 7/06; A01M 7/0089; B64C 39/024; B64C 2201/123; G01B 11/24; G01N 21/31; G01N 21/84; G01N 33/0098; G01N 2021/8466; G01N 2021/8416; G01N 2201/0221; G01N 21/251; G06Q 50/02; G01J 3/2823
See application file for complete search history.

(56) References Cited

U.S. PATENT DOCUMENTS

| | | |
|---|---|---|
| 2009/0160951 A1 | 6/2009 | Anderson et al. |
| 2015/0178546 A1 | 6/2015 | Abramovich et al. |
| 2015/0181139 A1* | 6/2015 | Kerbiriou ............ H04N 5/2354 |
| | | 348/297 |
| 2017/0118925 A1* | 5/2017 | Noguchi ................... G01J 3/42 |
| 2017/0192226 A1 | 7/2017 | Eineren et al. |
| 2020/0088509 A1* | 3/2020 | Reusch ................ G01B 5/0035 |
| 2021/0033716 A1* | 2/2021 | Choi ........................ G01S 13/46 |

FOREIGN PATENT DOCUMENTS

| | | |
|---|---|---|
| WO | 2016/124950 A1 | 8/2016 |
| WO | 2017/066927 A1 | 4/2017 |

OTHER PUBLICATIONS

Feris R et al: "Specular reflection reduction with multi-flash imaging", Computer Graphic and Image Processing, 2004, Proceeding 17th Brazil IAN Symposium on Curitiba, PR, Brazil Oct. 17-20, 2004, pp. 3160321.

* cited by examiner

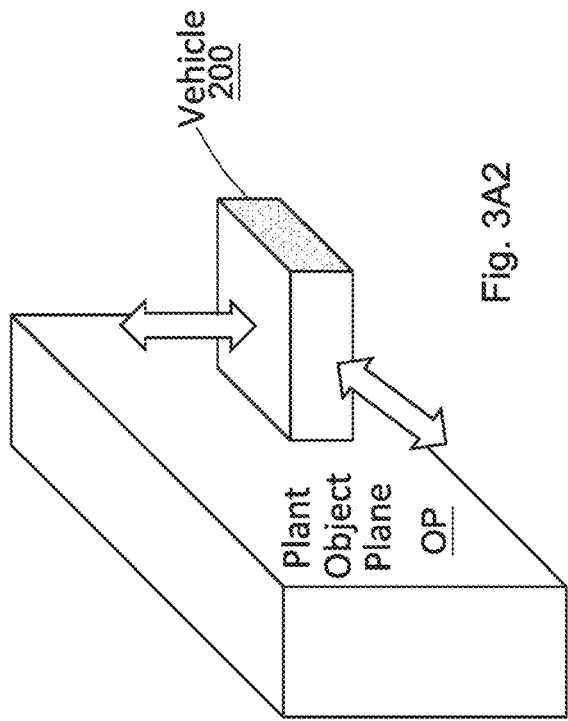
Fig. 3A2
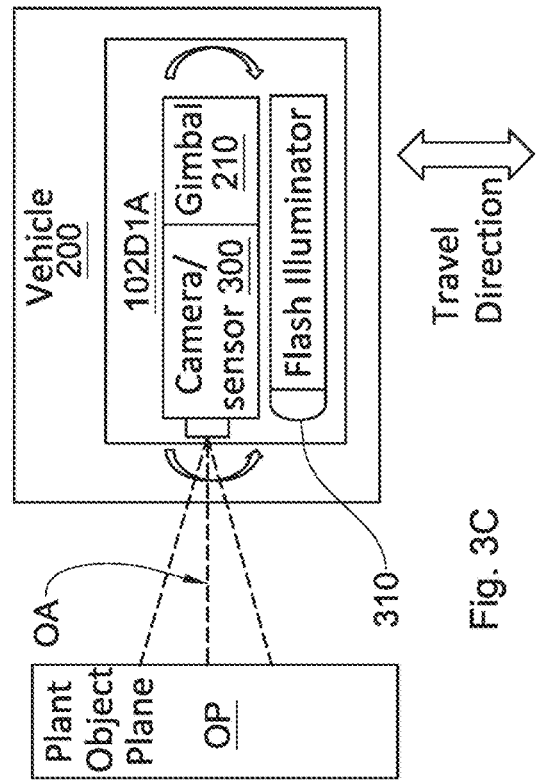
Fig. 3C
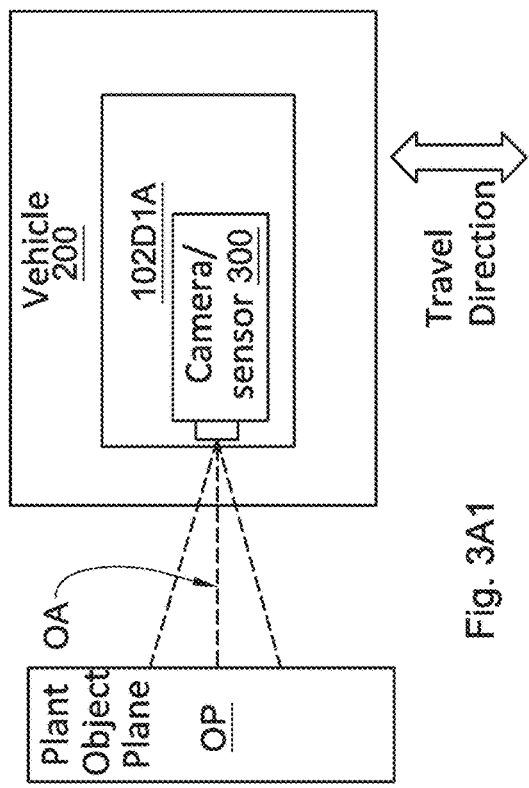
Fig. 3A1
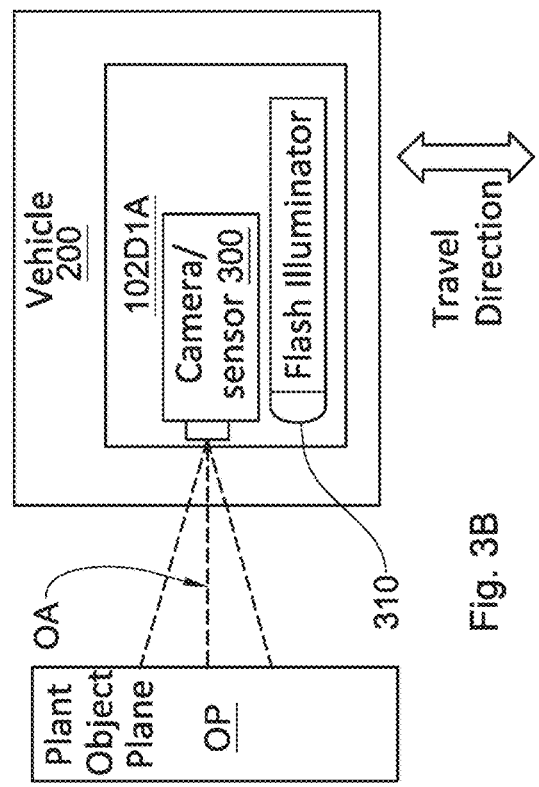
Fig. 3B

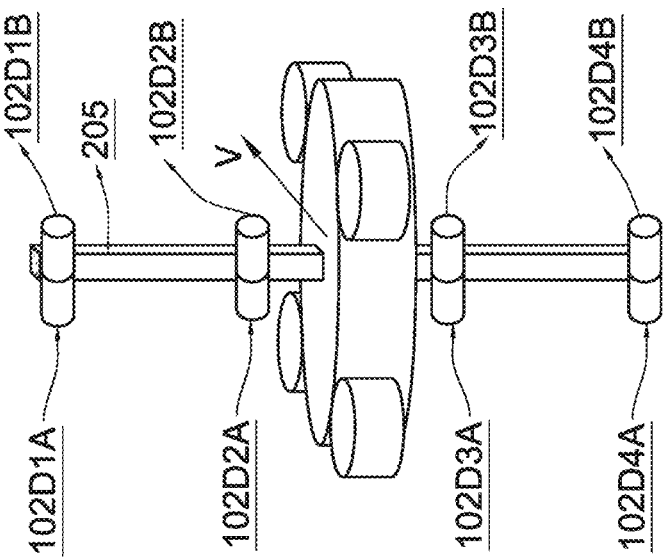
Fig. 4A2
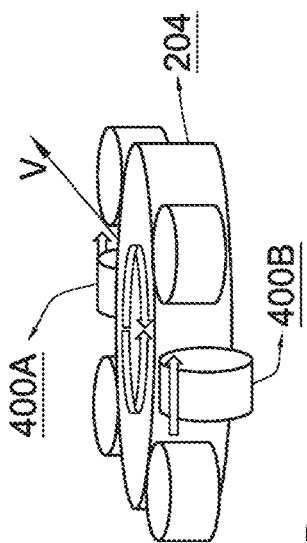
Fig. 4B
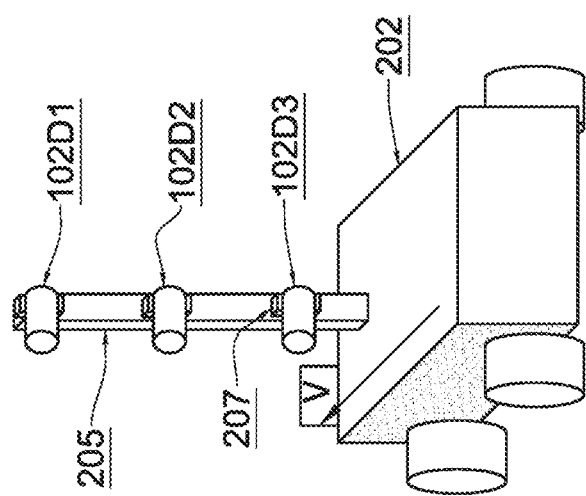
Fig. 4A1

SYSTEM AND METHOD FOR MONITORING PLANTS IN PLANT GROWING AREAS

TECHNOLOGICAL FIELD

The invention relates generally to the agricultural field, and more specifically to automated systems and methods of monitoring of plants and/or plant treatment decisions in plant growing areas.

BACKGROUND

Crops require a lot of care, either when grown in protected environment (such as in a greenhouse) or outdoors, especially when cultivated on a large scale where farmers continuously face a variety of challenges, including the need to maintain plants' health over the whole plant life cycle, control over flower pollination, and insure healthy as well as good yield crops. Indeed, it can be a difficult task to know whether the crop, at a specific time point, suffers from a problem, such as existence of pest, disease, or nutritional deficit, and what is the extent of the problem until it is readily visible. Often by that stage, it may require expensive and extensive intervention. Crop yield is affected by the physiological performance of the crop throughout its development cycle. Precise intervention at critical developmental stages, allows farmers to achieve high yields of the crop. A common practice for monitoring crops for pests, diseases and other deleterious conditions, has been the use of human scouts who visually inspect the crop. However, human inspection might take a long time, especially in large plant areas, and might facilitate the spread of those pests and diseases, for example, through physical contact with multiple plants, and is subject to subjective interpretation of the inspecting person.

Many crop management practices are employed based on past practices. A common underlying assumption is that crops are uniform and perform evenly which is not necessarily the case.

Sensor systems have been developed for crop monitoring. For example, some systems use a grid of sensors suspended above the crop or which fly over the crops. Handheld devices are also used to capture data from individual plants. Other systems rely on visual detection by means of motion detection or visual pattern recognition.

Some sensor systems are directed toward specific indicators (presence of disease, emergence of pests, etc.) with narrow spectra of responses. For example, fluorescent measurement systems have been used to detect far red spectra produced by plants when exposed to blue or red light. Conventional fluorescent measurement requires complex equipment, and typically a single assessment takes several minutes. Other sensory systems can collect very general information (temperature, humidity) that cannot accurately pinpoint problems at the level of individual plants.

GENERAL DESCRIPTION

The present invention provides novel systems and methods for monitoring plants' conditions in one or more plant growing areas, enabling management of crops, for example in greenhouses or open fields. The technique of the invention enables high quality, yet cost effective and time saving, autonomous monitoring and management of plant condition by utilizing different novel modules that collect data from a crop area, and individually characterize and determine the status of each plant, including plant health, growing stage such as flowering and fruitage, detrimental conditions such as pest infestations, diseases and environmental deficiencies. The invention also enables performing analysis of the plant condition and generating corresponding relevant recommendations for interventions. While being capable of managing each individual plant, the invention is particularly useful in managing large/multiple farming areas due to the highly effective data collection and analysis techniques.

According to the technique of the invention, the data collected includes image data mainly, but not only. The image data is collected in one or more data collection phases by one or more data collection module types being different in their specifications.

Thus, according to a broad aspect of the invention, there is provided an automatic system for monitoring plants' conditions in one or more plant growing areas, the system comprising:

a data collection system configured and operable to provide characterization data about plants in said one or more plant growing areas, the data collection system comprising data collection modules of at least first and second different types, the first type data collection module comprising a first imaging device of predetermined first optical properties and the second type data collection module comprising a second imaging device of predetermined second optical properties different from the first optical properties, the characterization data provided by at least one of the first and second imaging devices being indicative of various parameters of the plants being imaged; and a control system configured and operable to be in data communication with an analyzer to be responsive to operational data received from the analyzer and being based on analysis of the image data indicative of one or more plants being imaged by the first type imaging device, to selectively activate the second type imaging device to apply the second type imaging to at least a part of said one or more plants.

The first and second optical properties are different in field of view and resolution. More specifically, the second field of view and second resolution of the second type imaging device are, respectively, narrower and higher than first field of view and resolution of the first type imaging device. Thus, the first imaging device is referred to herein below as a wide-area imaging device (meaning it has a field of view wider than that of the second imaging device), and the second imaging device is referred to herein below as a high-resolution imaging device (meaning it has a resolution higher than that of the first imaging device).

For example, the wide-area field of view is chosen to be as wide as possible in order to minimize the number of images needed to cover the crop, with the limitations being distance from the camera to the object and the minimum required resolution. If the distance from the camera to the object is about 0.5 m, and a lens with 90 degrees angular field of view can be used, then the diagonal field of view on the object will be 1.0 m. If the minimum required resolution for imaging of plant parts is 0.5 mm, and an imaging sensor with 3 micron pixels is used, and the resolution of the optics, measured for example by line-spread-function or other relevant parameter, is 1.5 camera pixels, then magnification of $1/110=(3\times1.5)/500$ is required to provide the field-of-view at the required resolution.

The high-resolution is defined by the number of image pixels needed to resolve, detect and classify the smallest expected object. For example, an insect 0.5 mm in size may require about 30×30 resolved pixels in order to be analyzed, therefore an effective resolution of about 17 microns is required. If an imaging sensor with pixels 3 microns in size is used, and the resolution of the optics, measured for example by line-spread-function or other relevant parameter, is 1.5 camera pixels, then a magnification of about $1/3.8=(3\times1.5)/17$ is required from object to sensor in order to provide the high-resolution capability.

It should be noted that the control system may be a distributed system, i.e. functional utilities of the control system may be distributed between the collection modules or between one or more of the collection modules and a central station; or may generally be integral with one of the collection modules. It should also be noted that the analyzer may or may not be an integral part of the monitoring system. For example, the analyzer may be located at (installed in) a central station or can be a cloud-based service; or the analyzer may be integral with the control system; or functional utilities of the analyzer may be distributed between the monitoring system (e.g. the control system and/or data collection system) and a central station or a cloud-based server.

Specifically, characterization data collected includes one or more of the following, but is not limited to, whole plant images, leaf images, leaf underside images, flower images, plant crown images, fruit images, plant branch images, images of supporting wires and poles.

Characterization of the plant status may include one or more of the following, but is not limited to, detection and/or measurement of plant shape, plant height, leaf shape, leaf color, leaf discoloring, leaf orientation and linearity, pest insects, beneficial insects, fungi, insect generated liquid drops, insect webs, fruit size, fruit location and height from the ground, fruit orientation, fruit shape, fruit color and fruit ripeness.

In addition, one or more of the following can be saved in the system for use by the analyzer upon decision making: irrigation and fertilization data, date of planting, date of last harvest, dates of pruning and others.

Analysis of the plant condition by the analyzer may include one or more of the following, but is not limited to: generating information on the growing stage, and on the location and/or severity of detrimental conditions. The growing stage information may include plant height compared to plant age/growth cycle and plant height distribution; leaf size, leaf color and leaf density and distribution; flower density and distribution; fruit size, fruit color, fruit ripeness and fruit density and distribution; branch quantity and density. The detrimental conditions information may include fungus location and severity distribution; insect pest location and severity distribution; leaf deformation and severity distribution.

Analysis output from the analyzer may be in the form of tabular data, density maps of parametric data, maps with embedded data such as photographs, recommended treatment maps such as beneficial type and density for spreading and insecticide type and spraying parameters.

In some embodiments, the data collection modules are configured and operable to be in data communication with the analyzer, for communicating the characterization data to the analyzer, thereby enabling generation of output data indicative of plant status for each plant being imaged, based on analysis of the characterization data. The output data comprises data indicative of a predetermined condition of one or more plants being imaged by at least one of the first type and second type imaging devices. The operational data may further include recommendation data to a plant growth control system.

Recommendation data to a plant growth control system may include interventions that may relate to one or more of the following, but is not limited to, insecticide spraying, beneficial spreading, irrigation planning, fertilization planning, fruit picking, fruit pruning, leaf and branch pruning, inspection planning, treatment type for detrimental condition taking into account presence of beneficial species. The recommendations may relate to the whole cultivated area or to local requirements in a subsection of the cultivated area, or to a more than one cultivated area.

Interventions/Treatment actions may include insecticide spraying, beneficial biological agent distribution, pruning of leaves and branches, picking of fruit, thinning of fruit, and fertilizer spreading.

As described above, the control system is configured and operable to selectively activate the second type imaging device to apply the second type imaging to at least a part of said one or more plants. In some embodiments, the control system is further configured and operable to perform one or more of the following: activate imaging sessions of the first and second type imaging devices to be performed at least partially simultaneously; and selectively adjust a movement path of the second type imaging device during an imaging session, based on the image data obtained by the first type imaging device prior to or during said imaging session performed by the second type imaging device.

The data collection modules are configured and operable to be in data communication with the analyzer, for communicating the characterization data to the analyzer, thereby enabling generation of output data indicative of plant status for each plant being imaged based on analysis of the characterization data. The output data includes data indicative of a predetermined condition of the one or more plants being imaged by at least one of the first type and second type imaging device. The operational data may further include recommendation data to a plant growth control system.

The analyzer may be configured and operable to analyze the first type image data obtained in a certain imaging session performed by the first type imaging device by comparing the first type image data to pre-stored image data obtained in one or more preceding imaging sessions performed by at least one of the first and second type imaging devices.

The analyzer may be configured and operable to analyze at least one of the first and second type image data and determine one or more suspect locations within the at least part of the plant growing area. The control system and/or analyzer may be configured and operable to determine at least one movement path for at least one of the first and second type imaging devices to access the one or more suspect locations.

In some embodiments, the system is configured and operable to utilize the image data obtained by at least one of the second type imaging devices to optimize (improve the quality of) analysis of the image data provided by at least one of the first type imaging devices.

In some embodiments, the control system and/or analyzer is configured and operable to analyze image data indicative of multiple overlapping images obtained by at least one of the first type imaging device and second type imaging device in the plant growing area and generate three-dimensional plant shape data associated with said plant growing area and including at least some of: leaves, branches, stalks, flowers and fruit of the plants in said plant growing area. The multiple overlapping images may comprise at least one in-focus image and at least one out-of-focus image obtained by said at least one of the first imaging device and second imaging device. The control system and/or analyzer may be further configured and operable to analyze the three-dimensional plant shape data and determine one or more suspect locations in the plant growing area.

The system preferably includes one or more vehicles carrying the data collection modules. At least one of the vehicles may carry at least one of the first type and second type collection modules; and/or the first type and second type collection modules may be carried by first and second vehicles, respectively. One or more vehicles may comprise at least one of unmanned aerial vehicle and unmanned ground vehicle.

In some embodiments, the analyzer is configured and operable to carry out the following: process at least one of the characterization data provided by the first type imaging device and three-dimensional plant shape data associated with said plant growing area and determine one or more of the following plant characteristics: plant structure, plant height, plant biomass, leaf color, leaf outline including at least one of leaf size, leaf angle, leaf shape and leaf distortion, fruit size, fruit location and height from the ground, fruit orientation, fruit shape, fruit color and fruit ripeness, flower location and height from the ground, flower orientation; and analyze said one or more determined plant characteristics in accordance with the one or more predetermined conditions to perform said selective generation of at least one of the operational data to activate the second type data collection module and the recommendation data to the plant growth control system.

The analyzer may be further configured and operable to be responsive to the characterization data contained in the second type image data, and upon determining that one or more parameters of the plant correspond to one or more predetermined conditions, generate the recommendation data to the plant growth control system. Such parameter(s) of the plant determined from the second type image data may include one or more of the following: leaf shape, leaf color, leaf discoloring, pest insects, beneficial insects, fungi, insect generated liquid drops, insect webs, and diseases.

In some embodiments, the analyzer is configured and operable to utilize the parameters of the plants determined from at least one of the first and second type image data to provide output data indicative of at least a part of the plant growing area. The output data includes data indicative of one or more of the following: plant height compared to plant age/growth cycle, plant height distribution, plant biomass, leaf size, color and density distribution, fruit size, ripeness, color, density and height distribution, flower density and height distribution, branch quantity, density and height distribution, specific pest insects density, specific beneficial insects density, ratio of specific beneficial insects to specific pest insects, fungi density, and diseases density. The output data may comprise one or more of the following: tabular data, density maps of parametric data, maps with embedded data, recommended treatment maps.

The recommendation data may comprise at least one of the following: (i) treatment data indicative of a plant treatment plan including one or more of the following: insecticide spraying, beneficial insect spreading, irrigation planning, fertilization planning, fruit picking, fruit thinning, leaf and branch pruning, plant trellising; and (ii) environmental data indicative of an environmental condition change in the plant growing area.

In some embodiments, the control system and/or analyzer is configured for data communication with one or more plant growth modules of the plant growth control system to deliver said recommendation data, the one or more plant growth modules providing at least one of: insecticide spraying, beneficial spreading, irrigation planning, fertilization planning, fruit picking, fruit pruning, leaf and branch pruning.

The first type imaging device is configured and operable to perform an imaging session of the plant growing area with an optical axis essentially perpendicular to a row along which plants are arranged in a spaced-apart fashion. The system is configured and operable to operate said first type imaging device to perform said imaging session while moving along a movement path substantially parallel to said row. In some embodiments, the first type imaging device performs the imaging session while moving along said movement path with a varying height above ground. In some embodiments, the first type imaging device performs imaging of spaced-apart parallel rows of plants located on both sides of an aisle while moving along said movement path. In some embodiments, the data collection system is configured such that at least two of the first type imaging devices are mounted in a spaced-apart relationship on a vertical support being therefore arranged at different heights.

The system may include a flash illuminator associated with at least one of the first type and second type data collection modules. The flash illuminator may be configured and operable to provide a variety of illumination intensities and/or a variety of exposure levels for multiple image acquisitions of a plant with different illumination intensities and/or exposure levels, thereby optimizing three-dimensional modeling of the plant.

In some embodiments, the first type data collection module performs imaging sessions for plants in the row while performing relative movement with respect to the plant being imaged. The first type data collection module may comprise a flash illuminator configured and operable to provide at least one of pulse time and intensity of flash illumination selected in accordance with at least one of a velocity of said relative movement and a distance between the first type imaging device and the plant being imaged.

In some embodiments, at least one of the first type data collection modules and the control system is configured and operable to periodically vary a velocity of the relative movement such that the velocity drops down to below a certain value when an image capture is required.

In some embodiments, the first type data collection module comprises an angular motion mechanism, which is associated with at least one first type imaging device and is configured and operable to controllably rotate an optical axis of said at least one first type imaging device such that the optical axis is perpendicular to the plant being imaged during an image capture and the velocity of angular rotation of the optical axis compensates for the relative movement of said data collection module.

In some embodiments, the first type data collection module comprises an angular motion mechanism associated with a pair of the first type imaging devices accommodated such that their optical axes are parallel while pointing in opposite directions. The angular motion mechanism comprises a controllable oscillator configured and operable to perform controllable oscillation of said optical axes in an alternating fashion such that oscillation velocity compensates for the relative movement while maintaining the optical axes perpendicular to the plant during an image capture. The angular motion mechanism may further comprise a pair of light directing elements in the optical axes of said pair of the first type imaging devices, respectively, to redirect optical paths defined by the optical axes to opposite pointing directions.

The controllable oscillator may be associated with either the pair of the light directing elements or the pair of the first type imaging devices.

In some embodiments, an angular motion mechanism is associated with an imaging sensor of the first type imaging device for controlling oscillatory motion of said imaging sensor to compensate for the relative movement.

In some embodiments, an angular motion mechanism is associated with an imaging lens of the first type imaging device for controlling oscillatory motion of the imaging lens to compensate for the relative movement.

In some embodiments, the first type imaging device comprises a video camera operable with a certain video frame rate, and an angular motion mechanism is configured and operable to rotate the camera at a frequency corresponding to the video frame rate.

In some embodiments, the first type data collection module is carried by a drone, and an angular motion mechanism is provided for controlling angular motion of the optical axis of the first imaging device by intentionally controlled yaw of the drone.

The first and second types imaging devices may be configured and operable to perform imaging using one or more of the following illumination schemes: visual spectrum, IR spectrum, IR, multi-spectral imaging, exciting illumination causing fluorescence response of plants being imaged, exciting illumination causing fluorescence response of insects being imaged.

The invention also provides a method for managing operation of a plant growing area, the method comprising:

applying first type imaging to at least a part of the plant growing area while moving along said at least part of the plant growing area, generating first type image data comprising characterization data indicative of various parameters of plants being imaged in said at least part of the plant growing area, and communicating said first type image data to an analyzer;

in response to data received from the analyzer, selectively carrying out at least one of the following: (1) activating a second type imaging to be applied to one or more selective regions within said at least part of the plant growing area; (2) activating plant treatment procedure with respect to at least some regions said at least part of the plant growing area; and (3) affecting one or more environmental conditions within the plant growing area.

The invention further provides a control system for managing operation of a plant growing area, the control system comprising:

a plurality of unmanned vehicles controllably operable to travel within the plant growing area along multiple travel paths, wherein said plurality of vehicles carrying first type imaging devices of predetermined first optical properties and second type imaging device of predetermined second optical properties different from the first optical properties; and a control unit configured and operable to control operation of a first group of vehicles and a second group of vehicles to perform first and second type imaging sessions by said first type and second type imaging devices, respectively, according to predetermined first and second operational patterns, the operational pattern being defined by a motion pattern of the vehicle and an imaging mode of the imaging device.

The plurality of vehicles may be operable to travel simultaneously in the plant growing area and communicate with each other to aid in prevention of collisions.

The motion pattern to be used in an imaging session may be determined based on data including at least one of the following: imaging data collected in one or more preceding imaging sessions performed by at least one first and second type imaging devices; and data provided by an external information source.

The motion pattern of the second type imaging device may be periodically or continuously adjusted based on operational data determined based on data collected by the first type imaging device operating simultaneously with the second type imaging device.

The invention also provides a control system for use in monitoring plants' conditions in plant growing areas, configured for data communication with multiple automatic monitoring systems via a communication network and comprising an analyzer configured to be responsive to characterization data pieces received from multiple data collection modules and carry out the following, for each characterization data piece:

identify first or second type image data embedded in the characterization data piece and a respective plant growing area where said characterization data piece has been collected;

analyze said first or second type image data, and selectively generate at least one of the following: (i) based on analysis of the first type image data, generate operational data to a local control unit of a data collection module to activate second type imaging to be applied in at least a part of the respective plant growing area; and (ii) based on analysis of at least one of the first and second type image data, generate recommendation data to a local plant growth control system of said plant growing area.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIGS. 3A-3K illustrate non-limiting exemplary embodiments of first type imaging devices being wide-area imaging devices, in accordance with the present invention;

FIGS. 4A-4B illustrate non-limiting exemplary embodiments of the first type data collection module when including more than one first type imaging device, in accordance with the present invention;

DETAILED DESCRIPTION OF EMBODIMENTS

Figure 1:
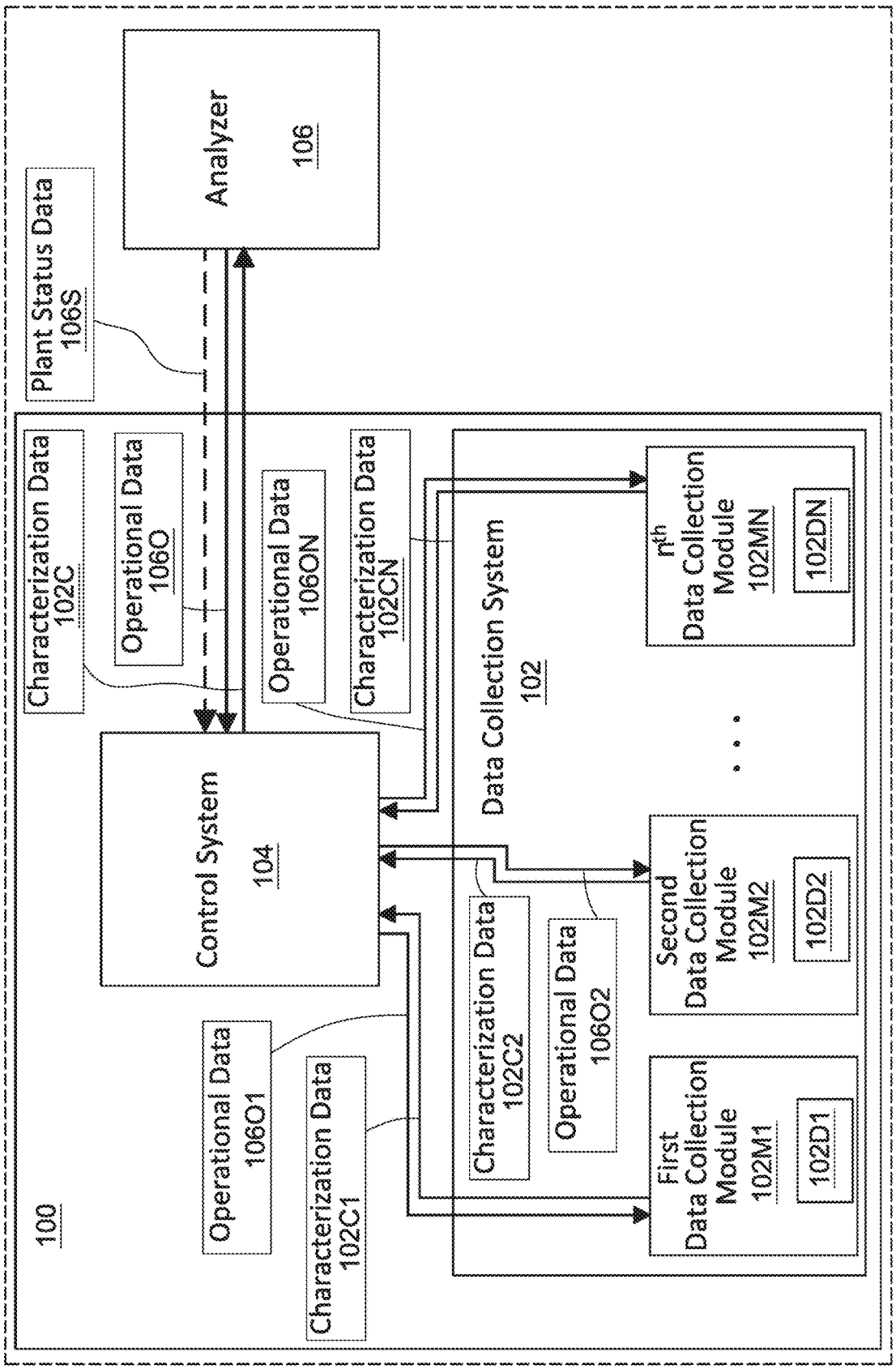
FIG. 1 illustrates, by way of a block diagram, a non-limiting exemplary embodiment of a plant inspection system, for monitoring plants' conditions in one or more plant growing areas, in accordance with the present invention.

Reference is made to FIG. 1 illustrating by way of a block diagram a non-limiting exemplary embodiment of a system 100 configured and operable for monitoring plants' conditions in one or more plant growing areas, in accordance with the present invention. As shown, the system 100 includes a data collection system 102 and a control system 104 being in data communication therebetween. The data collection system 102 is configured and operable to provide characterization data about one or more plants in the plant growing area(s) and send the characterization data to the control system 104. The control system 104 is configured and operable to receive data collected by the data collection system and control operation of the data collection system 102 by utilizing operational data received from an analyzer as will be described further below.

As illustrated, the data collection system 102 includes a plurality of (at least two) data collection modules 102M1, 102M2, ..., 102MN, configured and operable to measure certain parameters of the plant(s) and provide corresponding characterization data 102C1, 102C2, ..., 102CN, being indicative of various parameters of the plants being monitored. The data collection modules include such modules of at least first and second different types, where the first type data collection module 102M1 includes at least one first imaging device 102D1 having predetermined first optical properties, and the second type data collection module 102M2 includes at least one second imaging device 102D2 having predetermined second optical properties which are different from the first optical properties of the first imaging device 102D1. The first type imaging device is configured as a relatively wide-area imaging device (i.e. it has a field of view wider than that of the second imaging device), and the second type imaging device is a relatively high-resolution imaging device (i.e. it has a resolution higher than that of the first imaging device).

The characterization data provided by the first and second imaging devices, 102C1 and 102C2, are indicative of various parameters of the plants being imaged. Additional types of imaging devices, such as 102DN, may be optionally included in the data collection modules.

As appreciated, the data collection system 102 may include more than the two data collection modules, e.g. N data collection modules 102M1-102MN, as illustrated in the figure, configured and operable to provide N characterization data pieces 102C1-102CN, as will be further described below.

It is noted that the characterization data pieces collected by the data collection modules can also include information of at least some of the following parameters: image capture location spatial coordinates, image capture optical axis directional coordinates, and time of image capture.

The control system 104 is configured and operable to be in data communication with an analyzer 106 and to be responsive to the operational data 106O received from the analyzer 106. Specifically, the operational data 106O is based on analysis of the image data indicative of one or more plants being imaged by the first type (wide-area) imaging device 102D1, and is used by the control system 104 to selectively activate the second type imaging device 102D2 to apply the second type imaging to at least a part of said one or more plants and provide the characterization data 102C2. In some exemplary embodiments, as illustrated in the figure, the control system 104 is configured and operable to receive the characterization data 102C, generally originating from one or more data collection modules, and send the characterization data 102C to the analyzer 106. Specifically, the control system 104 is configured and operable to receive and send the characterization data 120C1 indicative of one or more plants being imaged by the first type imaging device 120D1 to the analyzer 106.

Alternatively, in some exemplary embodiments, while not illustrated in the figure, the data collection modules can be configured and operable to directly communicate with the analyzer 106 to send the characterization data 102C thereto, while the operational data generated by the analyzer are sent to the control system 104 to thereby selectively activate a specific data collection module in the data collection system 102. Either way, the different systems/modules include respective communication utilities enabling the various communications described above. The data communication between the different systems/modules is carried out according to suitable communication techniques known in the art and which do not need to be described in detail, e.g. via wired or wireless data communication.

As shown in the figure, the control system 104 is generally a computer system (hardware and software) configured and operable to communicate with the plurality of the data collection modules of the data collection system and with the analyzer. For example, the control system may be associated with a central system, and may be located in a central station while being configured to communicate with the data collection modules and the analyzer 106.

In some other exemplary embodiments, though not illustrated, the control system 104 may be a distributed system, such that each data collection module or each sub-group of data collection modules has its own control system associated therewith and being configured and operable between each data collection module or each sub-group of data collection modules and the analyzer 106. In the latter example, each such control system can be located in a local station while being configured to communicate with the corresponding data collection module(s) and the analyzer 106, or alternatively, each control system can be integral with each data collection module, sub-group of data collection modules, or imaging device.

In some exemplary embodiments, the central or distributed control system 104 is located in corresponding one or more work stations having a user interface enabling a user to review plant status data 106S or the operational data 106O received from the analyzer 106 and selectively and manually activate the second type imaging device 102D2 to apply the second type imaging to at least a part of said one or more plants and provide the characterization data 102C2.

The analyzer 106 does not necessarily form a constructional part of the system 100, as illustrated in the figure. The analyzer 106 can be located in a central station or can be a cloud-based service. The analyzer 106 is configured and operable to be in data communication (according to known techniques in the art) with the system 100 and more specifically with the control system 104. In some exemplary embodiments, the analyzer 106 can form part of the system 100, as illustrated by the dashed line in the figure. In such a case, the analyzer 106 may be integral with the control system 104, where both are located in a central station and configured and operable to communicate with the data collection system 102. In some other exemplary embodiments, the analyzer's functional utilities can be distributed such that some are integral with the control system 104 and some are located in a different central station or in a cloud-based server. In yet some other exemplary embodiments, at least some of the analyzer's functional utilities can be integral with the data collection system 102, and specifically with the first type data collection module to provide first stage analysis of the collected data thereby managing system resources and saving in overall data collection time. For example, the first type data collection module may be configured with analysis capabilities to provide immediate analysis of the first type images and discard those which are out-of-focus instead of simply transferring them to the control system/analyzer.

The analyzer 106 is configured and operable to be in data communication with the data collection module(s) or the control system, for receiving and analyzing the characterization data 102C and generating output data indicative of plant status 106S for each plant being imaged. Accordingly, the analyzer 106 is configured and operable for processing and analyzing the first image data 102C1 from the first type imaging device 102D1 and generating plant status data 106S, and upon identifying, based on the first image data, a predetermined condition of one or more plants being imaged by the first type imaging device 102D1, generating the operational data 106O to the control system 104 to activate either the first type imaging device again, or the second type imaging device to apply the second type imaging, to at least a part of the one or more plants. The analyzer 106 may also be configured and operable for processing and analyzing the first image data 102C1 from the first type imaging device 102D1 and the second image data 102C1 from the second type imaging device 102D1 and generating plant status data 106S. Again, as described above, activating the first and/or second image device can be subject to a user's decision upon review of the plant status data 106S. It is also noted that the plant status data 106S refers to a plant status determined by the analyzer 106 at any specific time and after analysis of any input from the data collection system 102, for example, the plant status data 106S can be updated by the analyzer after receiving and analyzing the characterization data 102C2 received from the second imaging device 102D2. Therefore, the plant status data 106S reflects the plant status in general and can refer, as the case may be, to the plant status after any specific analysis performed by the analyzer 106.

The analyzer 106 can also be configured and operable to receive and analyze the characterization data 102C2 from the second data collection module 102M2, or from any other data collection module and generate plant status data 106S. The analyzer 106 can perform analysis of the inputs and provide one or more outputs including: plant health status; pest recognition (quantification and location); disease recognition (quantification and location); plant structure (number and location of leaves, branches and fruits); flower characteristics and quantity; fruit health, ripeness, characteristics and quantity. The outputs may be in the form of tabular data, density maps of parametric data, maps with embedded data such as photographs, recommended treatment maps such as beneficial type and density for spreading and insecticide type and spraying parameters.

The plant status data, generated by the analyzer 106 based on characterization data from the first and/or second imaging devices, may include an image success parameter. The image success parameter may be based on image parameters such as sharpness of the image, resolution of the image at the object plane, percentage of area of the image in focus, absolute area in focus in the image, quality of illumination in the image, exposure level in the image, part of the plant which is in focus (e.g. flowers, fruit, leaves, tops of leaves, underside of leaves etc.), and others. A successful image may be defined based on an overall image success parameter above a certain threshold, or the image may receive a relative numerical score based on the aggregate of parameters, or the image may receive multiple success scores related to multiple parameters.

The success levels of the images in an area of plants can be analyzed by the analyzer 106 to obtain an area success parameter. The area may be a plant, a row of plants, the rows on two sides of an aisle, or any other area of plants as selected. The area success parameter may be defined based on the number of successful images within the area, on the distances between successful images in the area, on the number of successful images of a specific plant part in the area (e.g. number of successfully focused images of flowers), the distribution of successful images, the location of successful images, and others. If the area success level is below a certain threshold, the first and/or second imaging device may be brought to the same area to repeat image collection in at least part of the area, or the imaging device may collect images in new locations within the area.

The system 100 can include one or more vehicles that carry the data collection modules and bring the data collection modules 102M1-102MN to the desired location in the plant growing area(s), as will be further described below. In some exemplary embodiments, each vehicle carries at least one of the collection modules, being at least one of the first type and second types collection modules. In some exemplary embodiments, the first and second types collection modules, 102M1 and 102M2, are carried by first and second vehicles, respectively. In some exemplary embodiments, the vehicles are at least one of unmanned aerial vehicle (UAV, drone) and unmanned ground vehicle.

The system 100 is configured and operable to be located in one or more plant growing area(s), e.g. in an open field or a greenhouse. In some exemplary embodiments, a plurality of data collection systems 102 are located in a plurality of plant growing areas, each data collection system is connected to the same central control system 104 and analyzer 106. In some exemplary embodiments, a plurality of systems 100, each including a data collection system 102 and a respective control system 104, are located in a respective plurality of plant growing areas, where all the systems 100 are connected to the same central analyzer 106.

Figure 2:
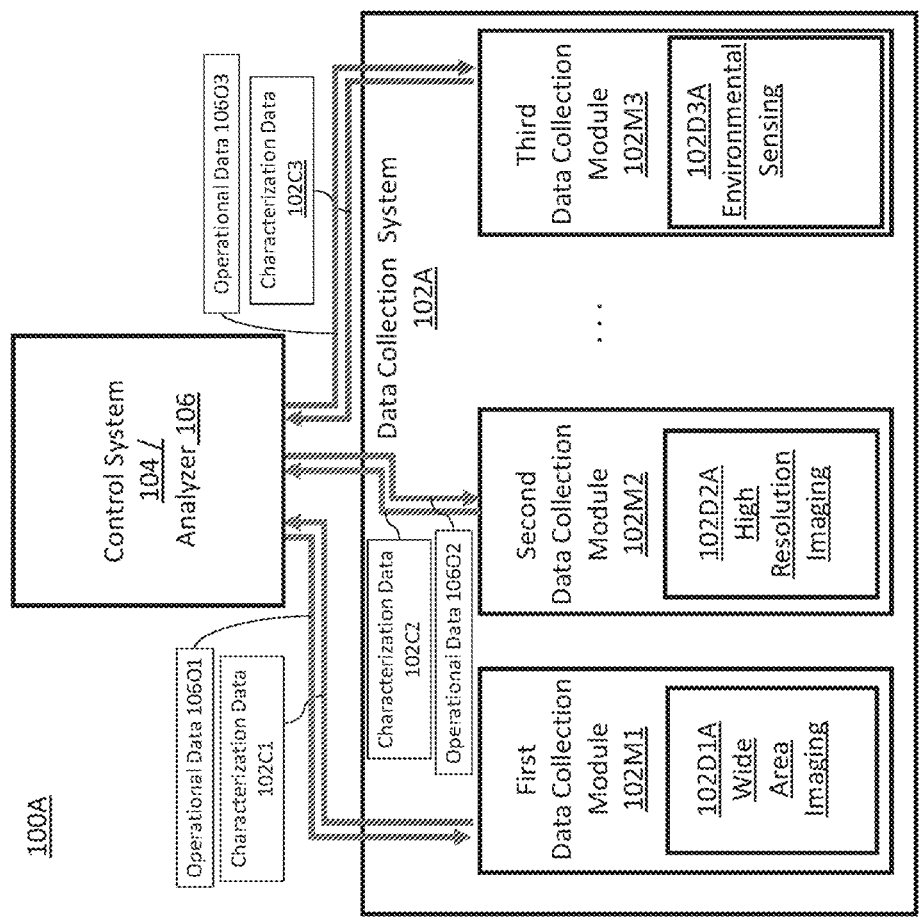
FIG. 2 illustrates, by way of a block diagram, a non-limiting exemplary embodiment of a data collection system, for monitoring plants' conditions in one or more plant growing areas, in accordance with the present invention.

Reference is made to FIG. 2, illustrating in more detail, by way of a block diagram, a non-limiting exemplary embodiment of a data collection system 102A configured and operable for monitoring plants' conditions in one or more plant growing areas, in accordance with the present invention. It is noted that apart from differences listed herein below, the data collection system 102A has similar functionality as the data collection system 102 described above with reference to FIG. 1.

As described above, the data collection system 102A is configured and operable to provide characterization data about one or more plants in the plant growing area(s) and send the characterization data to the control system 104. In this specific non-limiting example, as shown, the analyzer 106 is integral with the control system 104, where both can be located in a local or central station and configured and operable to communicate with the data collection system 102A to receive the characterization data 102C from the data collection system 102A and to send thereto, as needed, the operational data 1060.

The data collection system 102A, in this example, includes at least the first data collection module 102M1 and the second data collection module 102M2 that include respectively at least one first imaging device 102D1A and at least one second imaging device 102D2A, configured and operable as partially described above. Optionally, as shown and as will be described further below, the data collection system 102A also includes a third data collection module 102M3 including at least one environmental sensing device (s) 102D3A configured and operable to provide characterization data 102C3 and receive operational data 106O3 as necessary.

The first imaging device 102D1A includes at least one wide-area imaging device (wide-area camera) and is configured and operable to perform imaging of at least one or more of the following plants' parameters: full height, imaging of the top of the plants, imaging the sides of plants and imaging of other aspects of the cultivated area, as will be described further below. The wide-area imaging device is configured to navigate the plant growing area such that it travels at a suitable distance beside, above or below the plants, for example along a row undergoing inspection, and captures multiple images in order to provide visual information of the plants, e.g. the plants in the row. When the height of the plants is above the height of the vertical field of view of the wide-area imaging device, the wide-area imaging device may perform multiple scans, e.g. along the row, while changing the height and/or angle between scans, in order to collect full imaging coverage of the full height of the plants. The wide-area imaging device may perform imaging of rows of plants on both sides of an aisle in parallel while traveling in the center of the aisle, thus reducing the number of scans required to collect the full imaging data. The wide-area imaging device may scan in a vertical motion while moving forward in an aisle, where multiple images are collected in an essentially vertically shifted direction, and a sequential series of vertically shifted images is collected at a next horizontal location, thus enabling full imaging coverage of the full height of the plants. Sequential images collected during vertical motion may overlap in the vertical axis and images at a similar height from consecutive horizontal locations may overlap in the horizontal axis. Alternatively, the vertical location of the wide-area imaging device may be varied periodically during a scan in order to perform a sampling pattern of the row of plants. The scan covers different vertical locations along the row but enables sampling the various parts of the plants at multiple locations along each row. For example, a sawtooth or triangular vertical pattern may be performed along the row. Thus, a single scan essentially samples all areas of the row while the overall number of scans of the plant is reduced, thereby increasing the number of rows scanned per unit of time.

In some exemplary embodiments, depending, among others, on the stage of growth, plant height and weather conditions, the scans can be performed for only part of the heights of the plant, for example: the top third of the plant, the crown of the plant and the height of ripening fruit.

The wide-area imaging device may be configured to capture visible light, near infra-red light, multi-spectral light, spectrally filtered light, and/or UV fluorescence. The light source may be selected from ambient light, and/or reflected flash illumination.

Additionally, in some embodiments, the first and/or second type imaging devices can be configured and operable to perform imaging using one or more of the following illumination schemes: visual spectrum, IR spectrum, IR, multi-spectral imaging, exciting illumination causing fluorescence response of plants being imaged, exciting illumination causing fluorescence response of insects being imaged.

In some embodiments, as described above, the wide-area imaging device (herein below referred to sometimes as "wide-area camera" or "camera") is located on one of unmanned aerial vehicle and unmanned ground vehicle that travels in parallel to the direction of the row and the at least one wide-area imaging device captures images with the optical axis essentially perpendicular to the direction of travel.

The distance between consecutive wide-area images may be smaller than the width of each image, enabling overlap of the images. Thus, with sufficient overlap, at least two images are captured of each element of the plants. The spatial reference data of each image can be recorded during image capture and may include the location of the imaging device in 3-dimensional space and the 3 axes of angular orientation of the imaging device, or a subset of these 6 parameters.

Wide-area images (the characterization data 102C1) collected from the wide-area imaging device during an imaging session performed during a run (movement) along a movement path at a specific side of a row undergo comparative analysis by the analyzer 106. The comparative analysis can include morphology, color of leaf and plant structure. For this purpose, the analyzer 106 may be configured as or include a machine learning system such as a neural network, where multiple categorized images of plants at various health states are used for the learning process. The analysis can automatically compensate for changes in lighting due to time of day and weather patterns.

The multiple viewing angles enable building a 3-dimensional model of each feature of the plant by the analyzer 106. A full 3-dimensional model of all the plants in a crop area may be generated. This model enables analysis of multiple characteristics of the plant for analyzing plant health status and also enables recognizing semi-hidden elements such as fruits and stalks of the plants.

In some embodiments, a 3-dimensional outline of each leaf is created from the at least two wide-area images. The leaf outlines are analyzed for leaf size, leaf angle, leaf shape and leaf distortion (including leaf curling). The 3-dimensional analysis enables separating the top side and the bottom side of the leaves. Combining the 3-dimensional information with the color information of the leaves enables separation of variations caused by lighting from variations caused by leaf discoloration.

In some embodiments, a 3-dimensional model of a plant or parts of a plant may be generated using at least one in-focus image and at least one out-of-focus image, where the 3-dimensional outline of the plant or parts thereof is created from at least two images including at least one out-of-focus image, and the details of the surfaces are created from the at least one in-focus image.

The plant shape information is analyzed by the analyzer 106 for detection of areas affected by disease, irrigation deficiency, fertilizer deficiency, and others, and the results of the analysis may be saved in a report for review by the user. Leaf shape and location may be analyzed and compared to a library of leaf distortions and locations, accessible by the analyzer 106, for detection of pests and diseases including viruses.

The analyzer 106 analyzes the plant information obtained from the wide-area images, for example, leaf outline and leaf color information, and defines suspect locations, usually leaves, that require further inspection.

The analyzer 106 may compare the information from the wide-area images to previous wide-area images from previous inspection runs. In cases where abnormalities where detected in previous runs in a specific area, the analyzer verifies whether additional changes to the plant have occurred. If further abnormalities have developed, the analyzer may define that specific area as a target to be examined again by the data collection system, by a human inspector or by other means. In the case that no further abnormalities have developed, the analyzer may still define the area as a target for examining the presence of beneficial insects or the effectivity of other treatment solutions, as will be further described below.

Based on the analysis of the characterization data 102C1 from the wide-area imaging device(s), the analyzer 106 may generate, as needed, operational data 106O1 for the wide-area imaging device, in the form of navigation data, for performing further scans of at least some locations of the plant growing area. The generation of the operational data 106O1 can be in real-time or between scan runs.

Additionally or alternatively, based on the analysis, the analyzer 106 may generate operational data 106O2 for the second data collection module 102M2 that contains the second type imaging device(s) 102D2A (high-resolution imaging device), to apply a second type imaging to at least some of the plants or portions of the plants that have been imaged by the wide-area imaging device. For example, the operational data 106O2 may include chosen leaves (and their locations) that are suspected of having disease or pests, and the second data collection module may be utilized to detect, verify or categorize the pest or disease affecting the leaf.

The analyzer 106 may detect multiple accessible plant parts, including leaves, underside of leaves, flowers, fruit and other plant parts, which may be approached by the first or second imaging device without encountering other plant parts. This enables inspecting multiple locations on the crop without coming into physical contact with the plant. This is of special importance when there is a need to prevent cross contamination between different areas of the crop to prevent spread of pests and diseases.

The operational data 106O2 may include navigation data, e.g. calculation of the preferred approach vector, for the second data collection module to use when entering the foliage of the plants, where the second data collection module approaches the target from a position and direction that enables an unencumbered approach for capturing images of stems, flowers, the underside and top side of the leaves and other plant parts. The analyzer 106 analyzes the location and shape of the leaves and defines navigation paths for the second data collection module to approach the more internal areas of the crops and access, for example, the plants' stalks. The operational data 106O2 transferred to the second data collection module may be in the form of at least one image, in the form of a 3-dimensional coordinate path, or a combination thereof, or any other format containing the required information.

The analyzer 106 can be configured to receive as input the geometrical dimensions and degrees-of-freedom of motion of the second data collection module and combine with the 3-dimensional model of the plant to extract accessible volumes which can be utilized by the second data collection module. Generally, the second data collection module may be an optical module for capturing images, measuring spectral characteristics or measuring other optical characteristics of the parts of the plant. The second data collection module may be an optical module with at least one camera for capturing images of pests, diseases or other detrimental conditions on plant parts.

Data from multiple wide-area inspection runs is collected throughout at least one growing season. Systematic variations of plant parameters (e.g. plant shape, leaf size, leaf shape, leaf color) in the plant vertical axis may be characterized. The data may be parameterized and used as a reference for typical characteristics of a growth season. During subsequent inspection runs, local deviations from systematic variation can be detected and correlated to specific deficiencies, pests and diseases.

As described above, the analyzer 106 may generate operational data 106O2 to selectively activate the second data collection module 102M2 by the control system 104.

The second imaging device 102D2A includes at least one high-resolution imaging device (high resolution camera) and is configured and operable to perform imaging of parts of the plants, mainly flowers, leaves, fruit and branches, with the aim of detecting small elements such as pests, diseases and beneficial insects. Accordingly, for example, the optical resolution of the high-resolution imaging device that enables satisfactory imaging of small insects and accurate recognition and classification, can be in the range of 1 micron to 100 microns. Such high-resolution images can enable detection, classification and mapping of the presence of detrimental conditions. Also, this enables analysis of the local ratio of beneficial insects to pest insects.

In order to detect many types of pests and diseases, it is preferential to perform imaging of the underside of leaves, as that is the preferred habitat of many such pests, especially at the early stages of the pest development. The underside of leaves is less accessible to imaging from a stand-off position, since plants grow with leaf upper side facing outwards and upwards towards solar illumination. Many pests are sub-millimeter in size, requiring high resolution of microns to tens of microns, in order to detect and classify the type of pest and its development phase (e.g. egg, larvae, adult). The underside of leaves of many types of plants is not a flat plane at the millimeter scale, requiring any high-resolution imaging solution to be able to cope with, for example, partially hidden pests along protruding veins or, for example, varying distances of different parts of the leaf from a flat focal plane.

The images captured by the high-resolution imaging device 102D2A are analyzed by the analyzer 106 for detecting presence of pests, diseases and beneficial insects. As such, the analyzer 106 may include an artificial intelligence module trained to recognize such pests, diseases and beneficial insects.

The target locations to be inspected can be provided by an external information source (e.g. the analyzer 106 that provides the operational data 106O2), can be chosen by the control system 104 or can be predetermined based on previous inspection history from the first or second data collection modules, or can be predetermined based on a path designed to provide effective statistical sampling of the plant growing area.

As described above, the analyzer 106 can be configured to analyze previously captured wide-area images of the plants and determine candidate locations that are considered suspicious for possible presence of pest or disease.

The wide-area imaging device and the high-resolution imaging device may be carried by the same or different vehicles.

As described above, the analysis of the wide-area images may define preferred targets and provide calculated navigation/access paths for accessing those targets. For example, navigation data, such as approach vectors, can be included with the operational data 106O2 for the high-resolution imaging device to inspect the targets while providing for minimum physical interaction with the plant.

In some embodiments, a series of wide-area images covering most of the areas of a row of plants is analyzed by the analyzer 106 for suspicious locations on plants which show a possible presence of pests, disease or other detrimental conditions. The analysis provides a series of preferred target locations which may include flowers, leaves, fruits and branches of different plants along the row. The analysis may provide information on an approach path for accessing the preferred targets. Furthermore, the analyzer may preferably select certain targets located in close proximity to enable inspection from one approach path. The analyzer may also provide an optimal sequence for inspecting the preferred targets. If the time required for inspecting the preferred suspicious targets is less than a predefined time, the analyzer may add additional targets to optimize a uniform coverage of the plant area up to a predefined maximum time.

The target objects may be defined in advance by the analyzer as part of an inspection path, where specific areas of the crop are defined for specific types of samples. For example, when inspecting a row of plants, the analyzer may define areas of the row where leaves are to be examined (in x, y, z coordinates), areas where fruit are to be examined, areas where flowers are to be examined and areas where branches are to be examined. Leaves may be examined on their top side, their bottom side or both. The procedure for automatically defining the areas to be examined may take into account the age of the plants, the height of the plants, previous history of findings on the plants, the season, the past weather history, the future weather forecast, the allotted time for inspecting the area of plants and other factors. The analyzer may preferably select locations where in a single approach, multiple targets may be accessed, for example a location where the top side of a leaf, a branch and a bottom side of a leaf can all be viewed from a single access path. The exact plant part to be inspected may also be determined autonomously by the data collection module with the high-resolution imaging device.

Images captured by the wide-area and/or high-resolution imaging device are typically stored in a database accessible by the system and can be utilized later for analysis and comparison.

If a disease or pest is found at the specified target, the approach images may be utilized by the analyzer for improving correlations between wide-area images of a plant and the locations in which diseases and pests are present. The images may include at least one of an image of the disease or pest, an image of the plant part containing the disease or pest, an image of the plant including the vicinity of the plant part. The quality of analysis of wide-area images by the analyzer may thus be continuously improved based on at least one image of the high-resolution imaging device. The quality of analysis of wide-area images by the analyzer may be further continuously improved based on at least two images with different field of view and resolution of the high-resolution imaging device.

The target information transferred to the high-resolution imaging device may be in the form of x-y-z coordinates, in the form of at least one target reference image, in the form of a 3-dimensional path, a combination thereof or any other format containing the required information.

In some embodiments, the high-resolution imaging device is carried by an unmanned vehicle which travels or flies in the area of crops, preferably along rows of crops, and is periodically brought into proximity to the plants in order to view flowers, leaves, fruit or branches. The analyzer may at least partially be located on the vehicle carrying the wide-area or high-resolution imaging device, or it may be located in a separate location while communicating with a controller on the vehicle.

In some embodiments, a vehicle with a wide-area imaging device performs inspection of an area of crops in a pre-defined path. A vehicle with a high-resolution imaging device, follows the wide-area imaging device in a pre-defined path with a pre-defined time lag in order to prevent physical contact between the vehicles. The path of the high-resolution imaging device may be divided into sub-sections and additional vehicles with high-resolution imaging devices may be allocated in each sub-section with appropriate time lags.

In some embodiments, the data from the wide-area inspection is analyzed by the analyzer and an additional augmented high-resolution inspection path is defined by the analyzer for the high-resolution imaging device to perform after completion of the pre-defined path.

In some embodiments, the wide-area data is continuously analyzed by the analyzer and where required, the analyzer defines a local augmentation of the high-resolution inspection path. The time lag between the wide-area imaging device and high-resolution imaging device is pre-defined to be sufficient to enable high-resolution imaging device path changes to be implemented in a forward location relative to the instantaneous location of the vehicle. The total inspection time of the high-resolution imaging device is thus increased by addition of the augmented inspection sections.

In some embodiments, the high-resolution imaging device performs the pre-defined high-resolution inspection path without interruption and maintains a minimal time lag behind the wide-area imaging device, while the additional augmented sections are performed by a second high-resolution imaging device which travels with a time lag in relation to the first high-resolution imaging device.

In some embodiments, the area to be inspected may be divided into sections, where a vehicle with a wide-area imaging device performs wide-area data collection of the sections. The wide-area data of the first section is analyzed, and a high-resolution data collection path is defined by the analyzer for a vehicle with a high-resolution imaging device, which enters the section and inspects it after the wide-area imaging device has moved on to a second section. The wide-area imaging device proceeds to inspect the second section, the wide-area data is analyzed and a path for the high-resolution imaging device is defined by the analyzer. The high-resolution imaging device performs inspection of the second section after the wide-area imaging device has moved to the third section. This cycle is repeated until all sections have been inspected.

Depending on the required time for performing the high-resolution inspection of a section, additional vehicles with high-resolution imaging devices may be operated simultaneously within each section in order to minimize the time lag between completion of the wide-area inspection and the high-resolution inspection of a section. The high-resolution inspection path can be divided into sub-sections in order to prevent overlap and possible physical contact between the vehicles of the high-resolution imaging devices.

In some embodiments, more than one vehicle with a wide-area imaging device may be operated in different sections, thus enabling a shorter inspection time of the inspected area. In each section one or more high-resolution imaging devices may be operated. Thus, multiple sets of wide-area and high-resolution imaging devices may be used in parallel to cover the area to be inspected.

In some embodiments, the high-resolution imaging device travels a pre-determined movement path of continuous scanning of the foliage at pre-determined heights and upon completion, receives from the analyzer coordinates of a path of targets based on information from a wide-area imaging device scan including specific flowers, leaves and other plant parts. The high-resolution imaging device may follow the path and capture images in continuous motion or capture images after stopping in proximity to the targets. The targets may also be determined by the analyzer using data collected during the pre-determined path of the high-resolution imaging device.

In some embodiments, the high-resolution imaging device receives coordinates of a path of targets from the analyzer based on information from a wide-area imaging device scan including specific flowers, leaves and other plant parts. The high-resolution imaging device may follow the path and capture images in continuous motion or capture images after stopping in proximity to the targets.

In some embodiments, the high-resolution imaging device travels along the foliage at a distance which enables continuous imaging of the plants and when a potential target is recognized, the high-resolution imaging device approaches the target and performs high-resolution imaging of the target location.

In some embodiments, the analyzer may determine the plant parts on which pests and diseases were found in images collected by a high-resolution imaging device and combine this information with imaging device coordinate information to provide the coordinates of plant parts with verified diseases and pests. The analyzer may then combine the coordinates of plant parts with verified diseases and pests, with the wide-area images collected of the same area to improve the disease and pest prediction based on wide-area images.

In some embodiments, wide-area and high-resolution imaging devices may be located on the same vehicle. At least one wide-area imaging device may be mounted on the vehicle and at least one high-resolution imaging device may be mounted on the same vehicle. In one embodiment, a high-resolution imaging device is located aft of a wide-area imaging device in relation to the vehicle's direction of travel. The imaging devices operate simultaneously, where the wide-area imaging device captures wide-area images of the plant from a distance, for example a distance of tens of centimeters, while the high-resolution imaging device captures high resolution images from a distance of centimeters, preferably at angles that enable imaging of the undersides of leaves and inside flowers. The high-resolution imaging device may include an optical probe which protrudes into the foliage of the plants. The wide-area images may be analyzed, and real time information may be provided for optimizing operation of the high-resolution imaging device, such as minimization of physical contact with fruit, stems or other parts of the plants. The information may be utilized for determining a preferred operation of the high-resolution imaging device to be used, for example to optimize the perpendicularity of the angle of the optical axis of the device in relation to the angle of leaves to be imaged. The information may also be used to perform rotation of the device to achieve improved perpendicularity. The information may be used to adjust the height of the imaging devices. The adjustments can be performed at a high frequency with short time lag, thus enabling continuous optimized high-resolution data collection without need for slowing down the forward motion of the vehicle.

In some embodiments, two wide-area imaging devices and two high-resolution imaging devices are located on the vehicle, enabling simultaneous imaging of two rows of plants on either side of the vehicle. The vehicle travels essentially along the middle of the aisle between the plants and the wide-area imaging devices image plants on both sides of the vehicle. The high-resolution imaging devices perform imaging of both sides of plants with information inputs from the wide-area imaging devices. The high-resolution imaging devices may consist of optical probes which protrude into the foliage of the plants on both sides of the vehicle. The length and angle of the optical probes may be adjusted to compensate for variations in the depth of the plants' foliage and for presence of stiff plant parts which are to be avoided. The information from the wide-area imaging devices is used to perform optimization of the operation of the two high-resolution imaging devices. The adjustments can be performed at a high frequency with short time lag, thus enabling continuous optimized high-resolution data collection without need for slowing down the forward motion of the vehicle. The data collection system 102A may include, as shown, a third data collection module 102M3 configured and operable to provide environmental data about the plant growing area. Accordingly, the third data collection module includes one or more environmental sensing devices 102D3A configured and operable to measure and provide environmental data such as: temperature parameters, air humidity parameters, wind direction and speed parameters, weather forecast, soil humidity parameters, sunlight parameters, soil nutrient parameters.

The environmental sensing devices 102D3A provide the environmental characterization data 102C3 to the control system 104/analyzer 106 which can analyze the data in order to, among others, plan the necessity/time/frequency/path of next inspection runs of the first and/or second imaging devices.

The analyzer 106 receives and analyzes the wide-area images collected by the wide-area imaging device during scans along the sides of rows, for determining characteristics such as morphology, shape and color of the leaf and plant structure. As mentioned above, the analysis may be performed by a machine learning system such as a neural network, where multiple categorized images of plants at various health states are used for the learning process. The analysis automatically compensates for changes in lighting due to time of day and weather patterns. The data may be compared to a database of known conditions for the specific type of plant; the data may be compared to the data collected on the same row in one or more previous runs (imaging sessions).

The analyzer 106 analyzes multiple types of input data received from the data collection system. As mentioned above, the inputs for analysis may include environmental data such as temperature, humidity, sunlight, lighting, shading, also including aggregated data over a history of the growth season and of previous seasons. The analysis can take into account characterization data and treatment data from infestations and diseases from previous occurrences and define an optimized treatment for the new occurrence.

The analysis output can include data on quantity, quality and location of flowers; quantity, color, size, quality, ripeness and location of fruit; location and shape of branches.

The analysis output can include calculation of height and biomass of each plant.

In plants, such as tomatoes, where in certain cases the stems are guided to grow at an angle from the base of the stem, the system merges data from multiple wide-area images to form a layout of each plant, including stems, leaves and fruit, and provide a biomass aggregate of each plant.

The analyzer's outputs can be provided in various formats including: tabular data, density maps of parametric data, maps with embedded data such as photographs, treatment recommendation maps such as beneficial type and density for spreading and insecticide type and spraying parameters, as will be further described below, and others.

The output may include recommendations to the user on changes in irrigation, fertilization, humidity, temperature, lighting, shading, branch pruning, fruit picking, fruit thinning, irrigation and fertilization plan changes and others. These recommended changes may be regarding adjustments to the parameter for the whole cultivated area or to a specific location in the inspected area. The output may also include recommendations for additional data collection by modules including but not limited to high-resolution imaging device, wide-area imaging device, multi-spectral imaging device, UV fluorescence imaging device and others.

The inspection results of multiple rows of plants may be transformed into a 2-dimensional map by placing inspection results of the vertical sides of the plants in a common plane. For two rows of plants which face each other across an aisle ("adjacent rows"), the results are represented in a single plane with the vertical data rotated into a single continuous plane such that the bases of the two rows meet along a line and the tops of the plants point away from each other. Two layers of plants which are located in the same row such that the distance between the plants is small ("adjacent plants"), are laid flat while placing the tops of the plants along a common line and the bases pointing away from each other. In such a representation, the 3-dimensional information is transformed into a 2-dimensional plane, whereby the length of the rows is equivalent to a first maximum dimension of the plane and the second orthogonal maximum plane dimension is equivalent to the number of rows multiplied by maximum row height multiplied by 2.

Data such as wide-area images of the full height of rows may be overlaid on the 2-dimensional representation.

Correlations may be carried out between adjacent rows and adjacent plants, and like conditions marked on common locations in parallel.

Reference is made to FIGS. 3A-3K schematically illustrating, in block diagrams, non-limiting examples of the wide-area imaging device, as a first data collection module, according to the present invention.

As mentioned above, generally the wide-area imaging device (camera) travels along a movement path extending along a row of plants, in parallel to the plants, with the optical axis of the wide-area camera pointing perpendicularly to the object plane of the plant, i.e. perpendicular to the movement path. This is illustrated in FIGS. 3A1-3A2. The wide-area imaging device 102D1A is mounted on a vehicle 200 (an unmanned ground or aerial vehicle) that is capable of moving along horizontal and vertical axes in parallel to the object plane. As shown in the figure, the optical axis OA of the camera/sensor 300 of the imaging device points to the left and is perpendicular with respect to the travel/movement path, as well as to the object plane OP of the imaged plant.

To minimize image smearing due to the forward motion, high speed flash illuminator 310 can be used, as illustrated in FIG. 3B. The flash illuminator 310 may be a part of the first type data collection module being associated with the wide-area camera. The flash illuminator 310 may be operable to provide certain pulse time pattern and/or intensity of the flash illumination selected in accordance with a speed/velocity of the movement and/or a distance between the wide-area camera and the plant being imaged.

In order to reduce the smearing below a required level, for example below 0.1 mm at the object plane, the effective sensor exposure time of the wide-area imaging device needs to be reduced with relation to the forward motion speed. The maximum flash illumination pulse time is determined by the equation:

$$dt = dX/V$$

where dX is the allowed smearing, V is the forward motion speed and dt is the maximum flash illumination pulse time.

The required intensity of the flash pulse is determined by one or more of the distance between the object and camera, plant reflectance, camera aperture, sensor size and other factors. In order to reduce the contribution of the ambient light to the image, the camera exposure time needs to be reduced below a level satisfying a condition that (camera exposure time*ambient light level at object plane)<<(flash pulse time*flash intensity at object plane).

This solution requires additional weight of the flash and the additional energy supply.

In some embodiments, the velocity of the forward motion of the camera/vehicle may be varied in an oscillatory manner by sequential acceleration and deceleration such that the forward velocity changes periodically, for example the velocity drops down to a certain value when image capture is required and increases between locations of image capture. The velocity may be varied in a sinusoidal oscillatory manner, in a triangular wave manner, in a sawtooth manner or in some other pattern of oscillatory motion. In some embodiments, the velocity variation may be combined with high intensity flash illumination, where the maximum pulse time requirement may be increased in inverse proportion to the reduction in speed.

In some embodiments, to minimize image smearing due to the forward motion, the optical axis of the camera may be rotated at a controlled angular rate in a direction opposite to the direction of forward motion about an axis essentially perpendicular to the axis of motion (movement path) and to the optical axis. The camera's optical axis angle may be varied in a sinusoidal oscillatory motion, in a triangular wave motion, in a sawtooth motion or in some other pattern of oscillatory motion, where the required angular velocity is achieved when the optical axis is essentially perpendicular to the row of plants.

As illustrated in FIG. 3C, an appropriate angular motion mechanism is provided to implement the above-described rotation of the optical axis of the camera 300. For example, the wide-area camera 300 can be mounted on such angular motion platform, for example on a gimbal 210, that enables rotation of the entire camera and accordingly the optical axis of the camera, as illustrated by the arrows, to enable the optical axis to be perpendicular to the object plane at the required angular velocity to minimize the smearing effect.

Figure 3D:
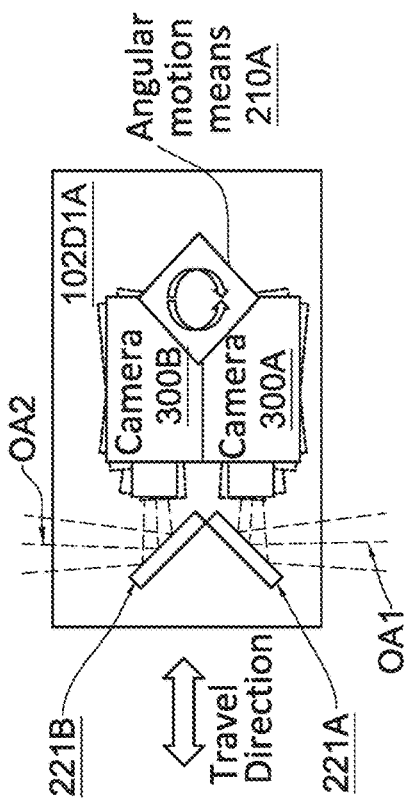

In some embodiments, as illustrated in FIG. 3D, instead of the rotation of the camera (e.g. by mounting it on the gimbal) or in addition to it, the angular motion mechanism is configured for rotation of the optical axis (i.e. an optical path defined by the optical axis). This can be implemented by using a moveable reflective/deflective optical element 220, such as a mirror, located in the optical axis of the camera, such that angular oscillation of the reflective optical element provides the controlled angular rotation of the optical path relative to the object plane.

The angular velocity of the optical axis rotation is appropriately selected to compensate for the smearing, whether by using a gimbal and/or a reflective optical element as illustrated above, which is determined by the velocity of the forward motion divided by the distance between the rotating element and the object plane. If the rotating element is a mirror or other reflective element, then the angular velocity to compensate for the smearing is determined by the velocity of the forward motion divided by the distance between the rotating reflective element and the object plane, divided by two.

The oscillating motion frequency is the forward motion velocity divided by the required spacing between images (image acquisitions/captures) in the forward motion direction.

In some embodiments, the oscillation of the camera angle may be utilized for compensation of image smearing when the camera/vehicle is operating between two rows of crops, where the camera oscillates through a wide arc larger than 180 degrees for sequential compensation of both rows on either side of the vehicle. During a first direction of rotation, the camera captures a motion compensated image of a first row. After crossing past the forward direction and during the opposite direction of angular motion, the camera captures a motion compensated image of the second row.

In some embodiments, one or more angular motion mechanisms (e.g. gimbal(s)) can be is association with two or more cameras, and the cameras optical axes oscillate together thereby enabling reduction of the range of angular oscillation. This may be that case that each camera faces a different row (i.e. optical axes of the camera point to different rows): the first camera captures an image of a first row, while a second camera captures an image of a second row.

Figure 3E:
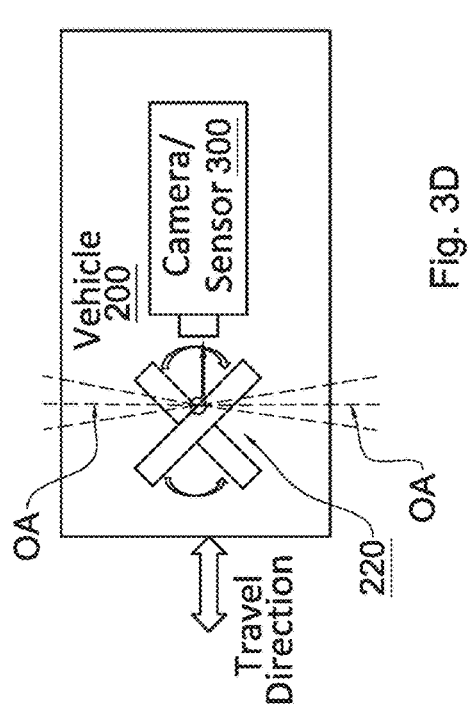

As illustrated in FIG. 3E, two cameras 300A and 300B, having respective optical axes OA1 and OA2 pointing in opposite directions (i.e. defining opposite fields of view towards oppositely located scenes), are connected to/associated with a single angular motion mechanism 210A. The cameras capture images of opposite rows in an alternating image acquisition pattern, i.e. during an image acquisition session a first camera 300A captures an image with appropriately correcting angular motion while the angular motion of the second camera 300B is in the non-correcting direction, and in a successive image acquisition session the second camera 300B captures an image with appropriately correcting angular motion when the angular motion of the first camera 300A is in the non-correcting direction. The angular motion mechanism may be a rotating gimbal or motor on which the at least two cameras are placed with their optical axes being parallel (substantially coinciding) but pointing in opposite directions.

Figure 3F:
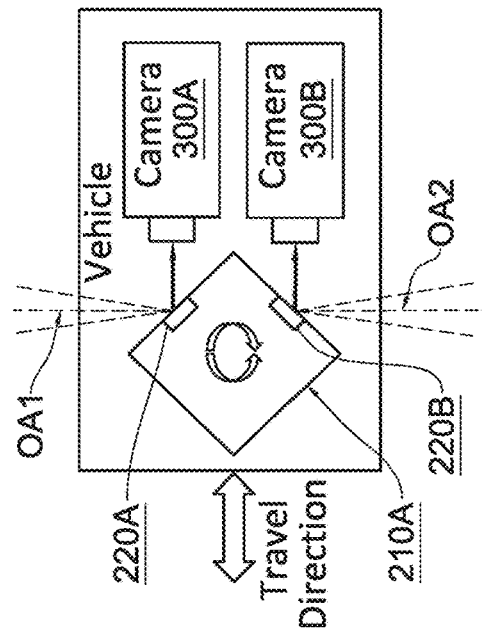

As illustrated in FIG. 3F, two cameras 300A and 300B are accommodated such that their respective optical axes OA1 and OA2 are arranged in a spaced-parallel relationship pointing in parallel directions. The cameras 300A and 300B are connected to/associated with a single (common) angular motion mechanism 210A, e.g. a rotating gimbal or motor, and respective static reflective optical elements 221A and 221B are located in the optical axes of the cameras and oriented with respect to the optical axes to deflect the respective optical axes to be perpendicular to respective plants. More specifically, the reflective elements redirect the optical paths defined by the optical axes such that the optical paths extend along the common axis but point to the opposite directions towards opposite rows. The angular motion mechanism oscillates and scans the optical axes angle. The cameras capture images of opposite rows in an alternating pattern when the optical path defined by the axis of each camera is perpendicular to the plant and the angular rotation velocity is in a compensating condition. This enables a more compact assembly than that illustrated in FIG. 3E.

Figure 3G:
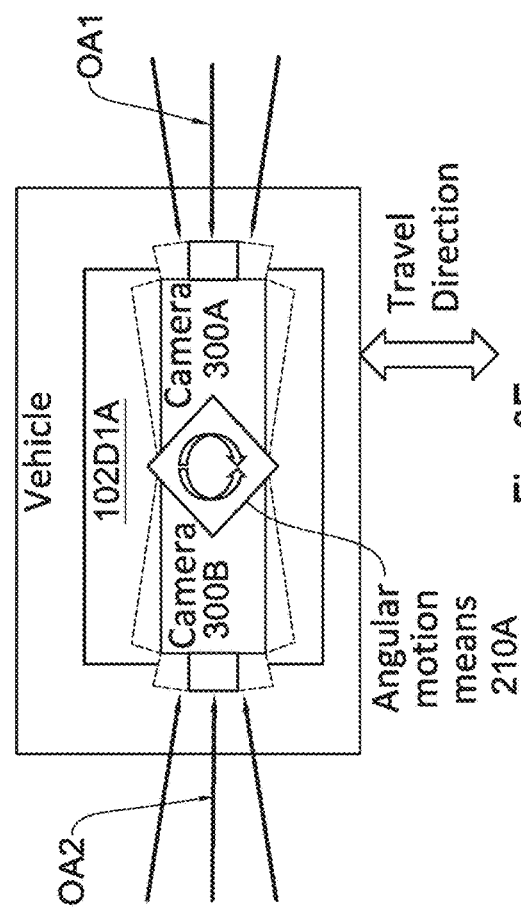

In some embodiments, as illustrated in FIG. 3G, the angular motion mechanism includes rotating reflective elements (e.g. mirrors) 220A and 220B associated with two cameras, respectively, and a common single axis oscillator turning in opposite directions in oscillatory manner. The two cameras are placed adjacent to each other, with their optical axes being arranged in a spaced-apart parallel relationship pointing to the parallel directions, intersecting with the respective reflective elements 220A and 220B each oriented at a 45-degree angle from its respective optical axis. The oscillator performs the angular correction with alternating timing between the two cameras. This enables a more compact assembly than that illustrated in FIG. 3F.

Figure 3H:
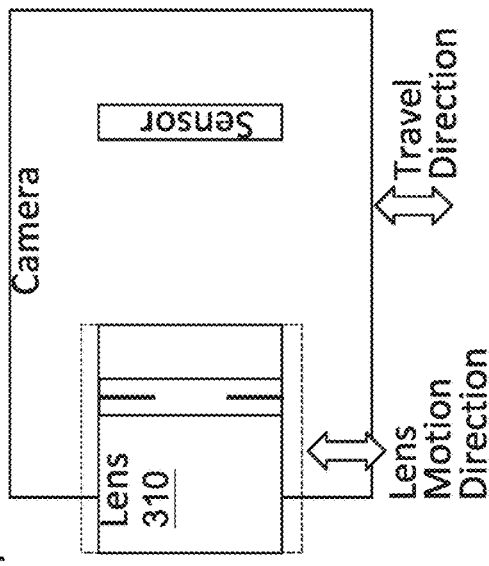

As illustrated in FIG. 3H, two cameras 300A and 300B may be placed in line facing each other, and the angular motion mechanism includes a rotating reflective optical element 220 located between the cameras in their optical axes (substantially coinciding) OA1 and OA2. The oscillating optical element 220 deflects the optical axes OA1 and OA2 of the respective cameras 300A and 300B, providing alternating image capture conditions where the optical axes are perpendicular to the plants with compensating velocity of angular rotation. This enables a narrower assembly than that illustrated in FIGS. 3E, 3F and 3G.

In some embodiments, each camera is separately paired with a separate oscillating mirror (not shown).

The camera exposure trigger (i.e. image acquisition pattern) is synchronized with the oscillation angle, where the orientation of the optical axis is essentially perpendicular to the row of plants and the angular velocity is nearly constant. For example, if the oscillator performs a sinusoidal angular scan, the point of maximal velocity in the correcting direction will be at the $\sin(\pi/2)$ point, with a velocity drop-off of under 5% in the range of $\pi/2+/-(5\%*\pi)$ radians. The required angular velocity is determined by the distance of the camera to the object plane and the velocity of the forward motion of the camera, where the amplitude of the oscillating motion is also determined by the required frequency of oscillation. In the case of sawtooth or other triangular oscillation profile, the connection between the angular velocity, frequency and motion amplitude may be reduced or decoupled.

Figure 3J:
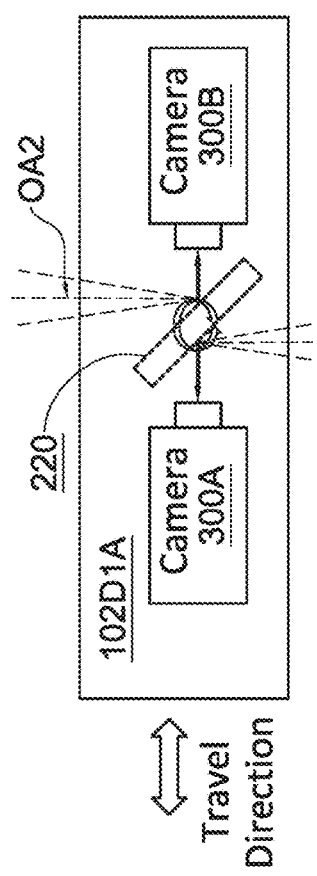
Figure 3I:
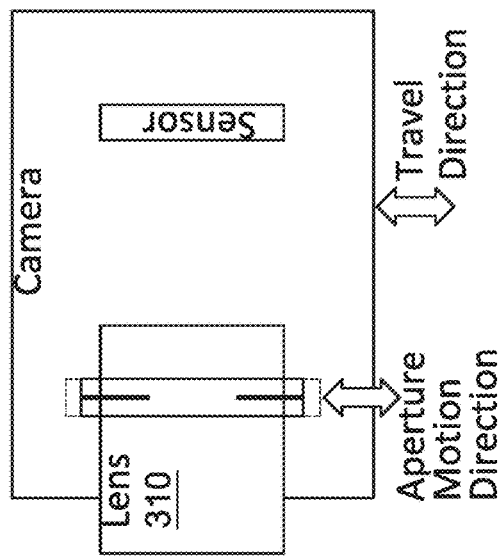

In some embodiments, as illustrated in FIG. 3I a lens 310 between the object and the camera sensor may be moved in an oscillatory motion in an axis compensating for the travel motion. The lateral velocity of the lens is determined by a ratio of the lens-aperture to sensor distance divided by the object to sensor distance multiplied by the forward motion velocity.

In some embodiments, as illustrated in FIG. 3J, the camera's sensor 320 (pixel matrix) is moved in an oscillatory motion in an axis compensating for the travel motion. The velocity of motion of the sensor is determined by the forward motion velocity multiplied by the magnification of the optical system of the camera.

Figure 3K:
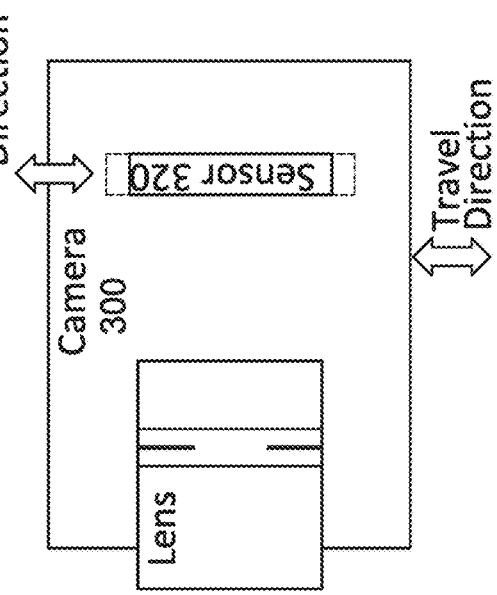

In some embodiments, as illustrated in FIG. 3K, the oscillator may be an aperture element of the camera placed in the optical axis and located at a Fourier plane relative to the camera sensor plane. The aperture moves parallel to the Fourier plane in the axis compensating for travel motion. The aperture's lateral velocity is determined by a ratio of the aperture to sensor distance divided by the object to sensor distance multiplied by the travel velocity.

In some embodiments, an optical image stabilizer module of any known suitable type may be used for producing a lateral compensating motion. In a case where the optical image stabilizer control is designed for compensating for camera angular vibration, a synthesized oscillatory signal is input to the pitch or yaw angular motion input of the stabilizer module, thereby producing a compensating lateral motion of the camera sensor.

In some embodiments, the at least one camera may be operated as a video camera with video frame rate. In this case, the oscillators are rotated at the video frame frequency, with a possibility to multiply the rotation frequency by an integer in order to meet angular range limitations. If the forward velocity and/or the distance to the object plane are changed, the maximal angular velocity, and therefore also the amplitude of the oscillator motion, are varied to compensate for the smearing, while maintaining the same frequency as the video. The forward motion distance between consecutive images will vary if the forward velocity changes. The forward velocity may be used as a parameter to vary the distance and a level of overlap between sequentially acquired/captured images.

In some embodiments, where smearing is reduced by compensating motion of the optics components or optical axis, flash illumination may be used to further reduce the image smearing.

Reference is made to FIGS. 4A-4B illustrating non-limiting examples of the first data collection module type when including more than one first imaging device type (e.g. a wide-area imaging device).

In some embodiments, as illustrated in FIG. 4A1, at least two first type imaging devices (102D1, 102D2, . . . ) are arranged on an unmanned vehicle (ground (202) or aerial (204)) being mounted on a vertical support/column/beam 205 in a spaced-apart relationship, i.e. at different heights. This enables simultaneous imaging of multiple locations at different heights of the plants on one side of the vehicle. The number of first type imaging devices may be varied according to the height of the plants, the available distance between devices and the plants, and the field of view of the first type imaging devices.

The height of the first type imaging devices may be adjusted by at least one height adjustment mechanism 207 (shown in FIG. 4A1) to obtain controlled overlap between the fields of view of the first type imaging devices. The heights and spacing between the first type imaging devices, and optionally the height of the vehicle, may be adjusted continuously or periodically by the height adjustment mechanism 207, based on information from the control system 104 and/or based on data analysis provided by the analyzer 106, in order to maintain required overlap between the captured images.

As illustrated in FIG. 4A2, the vertical support/column/beam 205 may be configured to carry two groups of vertically spaced first type imaging devices accommodated and oriented towards opposite directions to perform imaging of plants on both sides of the aisle, thus enabling collection of images covering the full height of all plants on both sides of an aisle.

In some embodiments, the wide-area camera is carried by a drone, where the angle rotation velocity of the camera's optical axis may be provided by intentionally controlled yaw of the drone. In a specific example of a multiple rotor drone, the yaw motion is introduced by changing the balance of torque provided by different rotors. In a standard controlled flight, the rotation moment around the central axis of rotation provided by the counter clockwise (CCW) rotating rotors is equal to the rotation moment caused by the clockwise (CW) rotating rotors. If the torque is increased on the CW rotating rotors, the drone rotates in the CW direction about its central axis of rotation. To generate the intentional yaw for correcting the image smear, the torque is raised and lowered in one of the CW or CCW sets relative to the other set in a cyclical pattern. Alternatively, the torque may be raised in one set of rotors, returned to normal, and then raised in the other rotor set, then returned to normal, and repeated in a cyclical pattern. For example, if the requirement is an oscillation with frequency of 25 Hz, an oscillating signal, preferably sinusoidal, is added to the motor supply of the CW rotors which raises and lowers the torque of the CW motors sinusoidally. This causes the drone to yaw periodically at this frequency.

In order to achieve the required angular velocity amplitude, the rotational inertia of the drone needs to be designed accordingly.

In some embodiments, as illustrated in FIG. 4B, instead of utilizing the standard rotors for yaw control, additional rotors (400A, 400B) may be added to the existing rotors. At least one pair of rotors may be added at the outer edges of the drone 204. The axes of the additional rotors are in a horizontal plane essentially perpendicular to, and at a radius from, the central axis of rotation, where the torque provided by the first rotor 400A creates a force which rotates the drone in the CW yaw direction while the second rotor 400B rotates the drone in the CCW yaw direction. The torque provided by the horizontal axis rotors is varied periodically in order to generate an oscillating net rotation force and thus an oscillating yaw about the central axis of rotation.

In some embodiments, two pairs of rotors are added, where one pair is added in the front of the drone and a second pair is at the aft of the drone. Within each pair of rotors, one rotor creates a CW force about the central axis of rotation and the second creates a CCW force. The torque provided by the horizontal axis rotors is varied periodically to generate an oscillating net rotation force and thus an oscillating yaw about the central axis of rotation.

In some embodiments, a rotatable weight is added above or below the drone, preferably near the central axis of rotation. The moment of inertia of the weight is designed to be relatively large in relation to the moment of inertia of the drone about the central axis of rotation. Rotating the weight, for example in a CW direction, will cause the drone to which it is attached to rotate in a CCW yaw direction.

In order to reduce drag to yaw motion, circumferential cowlings may be added around the rotors with a vertically neutral airfoil-like cross-section.

When the angle of view of the camera is large, additional considerations need to be made when calculating the optimal angular velocity for smear compensation. In this case, the distance between the camera and the plant row at the edge of the field of view, in the forward motion axis, is larger than the distance at the center of the image. The angular velocity calculated from the distance to the center of the image will be excessive in relation to the required correction at the edges of the image. Therefore a compensating angular velocity intermediate to the velocities calculated from the edge and the center will be used. The result will be a slight smearing over-compensation at the edges of the image and slight under-compensation at the center of the image. It should be understood that the effective exposure time is appropriately controlled, as the uncorrected angular smearing is multiplied by the effective exposure time. For example, the angular rotation correction may reduce the smearing at the center and edges of the image by an order of magnitude in relation to the same effective exposure time. Additional flash illumination may be provided to compensate for the uncorrected angular smearing.

Narrowing the width of the image in the forward motion axis reduces the differential smearing between the center and edge of the image.

The surface of the plant is a 3-dimensional structure. The technique of the invention enables imaging of different parts of the plant with different levels of illumination. In order to enable building an image with sufficient details on multiple plant surfaces, multiple illumination levels may be utilized, where different plant surfaces reach useable illumination levels at different exposures. This may be achieved by capturing multiple images, each with a different exposure time and/or different illumination intensity level. A preferred image may be chosen for further analysis based on maximal area with sufficient exposure, or properly exposed areas from multiple images may be combined into a composite image.

Also, different parts of the 3-dimensional surface of the plant may be imaged with varying exposure levels. In order to enable building an image with sufficient details on multiple plant surfaces, multiple exposure levels may be utilized, where different plant surfaces reach useable exposure levels at different conditions. Similarly, this may be achieved by capturing multiple images, each with a different exposure time and/or flash illumination intensity level. A preferred image may be chosen for further analysis based on maximal area with sufficient exposure or properly exposed areas from multiple images may be combined into a composite image.

The exposure level may be varied step-wise in a systematic manner. For example, if 3 levels of exposure are required, images n, n+3, n+6, . . . are set to a first exposure level, images n+1, n+4, n+7, . . . are set to a second exposure level and images n+2, n+5, n+8, . . . are set to a third exposure level. The multiple images may be captured with a shortened delay between images creating overlap, enabling building a composite image from multiple images with essentially the same field of view. In some embodiments, where the imaging utilizes oscillations to compensate for smearing, a series of images at different exposure levels may be captured during each cycle when the angular velocity is in sufficient compensating condition. For example, if the oscillation is sinusoidal, images taken within a narrow band about the peak angular velocity, may be captured within −5% and +5% of the optimal angular velocity as described above.

The image capture frequency may be set to enable the distance between consecutive images during motion to be smaller than the width of each image. This enables utilization of a subset of the images with a specific exposure level while providing coverage of the full area of the plants. This may also enable building a 3-dimensional model of the plants with multiple effective exposure levels of each part of the plant. Plant parts which are located deeper within the foliage may thus be imaged with sufficient exposure level at specific angles, enabling building a more complete 3-dimensional model of the plant. An improved quality 3-dimensional model of the plants may be built using multiple images from multiple angles and with multiple levels of exposure.

The exposure levels of the captured images may be analyzed during operation, for example at the start of an imaging session with respect to a row of plants, and adjustments may be made to the exposure levels and/or to the number of exposure level steps for the subsequent images in the imaging session. The analysis of the images may be performed by a processor located on the vehicle performing the imaging or on a local or remote station communicating with the vehicle. The factors which may affect the required levels of exposure may include distance from plants, depth of foliage, density of foliage, ambient light, surface reflectivity of parts of the plants, angle of optical axis, angle of illumination and others.

The variation in level of exposure may be achieved by varying the exposure time, peak intensity level of the illumination pulses, by shortening the length of the illumination pulses, by shifting the delay between exposure time and illumination pulse or by changing both the length and the peak level of the pulses.

The 3-dimensional model of the plant enables forming a 3-dimensional layout of the branch topology. The branch topology is mapped and analyzed by the analyzer 106, and operational data indicative of optimal locations for execution of branch and leaf pruning and trimming can be defined for achieving optimal plant growth and maximal production output of the crop. The information for pruning and trimming may be transferred to a plant growth control system, as will be described further below, or to a separate system for autonomous branch and leaf pruning, where the system utilizes the information for pruning specific branches and leaves. In some embodiments, the system for autonomous pruning may receive the 3-dimensional layout of the branch topology and define the optimal trimming locations independently. In some embodiments, the system for autonomous pruning may utilize a wide-area imaging device of the invention and detect and define the branches to be pruned independently.

The 3-dimensional model of the plant also enables forming a 3-dimensional fruit map of the location, size, color, ripeness, and density of fruit in the crop area. The fruit map is analyzed by the analyzer 106, and operational data indicative of optimal locations for fruit thinning can be defined for achieving optimal plant growth and maximal production output of the crop. The information for fruit thinning may be transferred to a plant growth control system, as will be described further below, or to a separate system for autonomous fruit thinning, where the system utilizes the information for thinning specific fruit. In some embodiments, the system for autonomous fruit thinning may receive the 3-dimensional fruit map of the fruit and define the optimal thinning locations independently. In some embodiments, the system for autonomous fruit thinning may utilize a wide-area imaging device of the invention and detect and define the fruit to be thinned independently. The 3-dimensional fruit map is analyzed by the analyzer 106, and operational data indicative of optimal locations for fruit picking can be defined for achieving optimal and maximal production output of the crop. The information for fruit picking may be transferred to a separate system for autonomous fruit picking, where the system utilizes the information for picking specific fruit. In some embodiments, the system for autonomous fruit picking may receive the 3D layout of the fruit and define the optimal picking locations independently.

The 3-dimensional model of the plant may also include 3-dimensional information on the poles, wires and strings supporting the plants. The analysis by the analyzer 106 can include recording of support pole locations and angles; guide wire continuity, location and angles; relation between guide-wires and branch locations. A 3D layout of the supporting structure may be formed and analyzed, and inconsistencies in the distribution and shape (e.g. sag) may be detected. A map of required corrective actions may be provided for the user. The information may be further processed and specific locations may be provided to a high-resolution imaging device of the invention for verification of issues.

Figure 5:
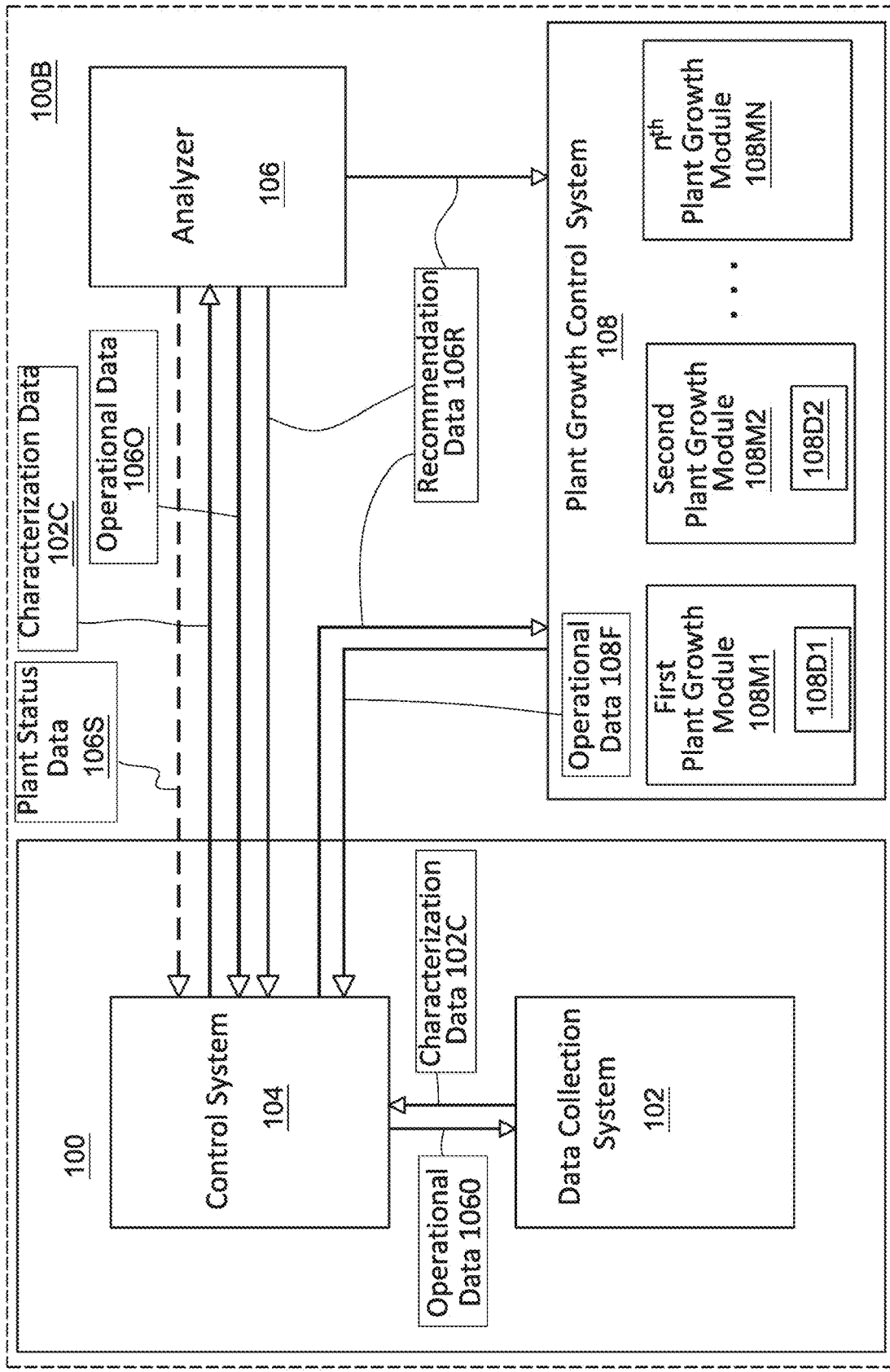
FIG. 5 illustrates, by way of a block diagram, a non-limiting exemplary embodiment of a plant growth control system, for controlling growth of plants in one or more plant growing areas, in accordance with the present invention.

Reference is made to FIG. 5, illustrating, by way of a block diagram, a non-limiting exemplary embodiment of a system 108 configured and operable for controlling plant growth in one or more plant growing areas, in accordance with the present invention. The plant growth control system 108 is configured for example to apply a treatment or distribute beneficial insects to plants, as will be described below.

The system 108 is configured to be in data communication with the analyzer 106 either directly or indirectly through the control system 104, as shown in the figure, to receive recommendation data 106R for controlling the plant growth in the growing area(s), where the recommendation data is generated by the analyzer 106 based on the analysis of the characterization data 102C (any characterization data received from any one of the data collection modules of the data collection system), as described above.

It is noted that the plant growth control system 108 can form an integral part of the system 100 or 100A described above, or can be a separate system configured and operable to communicate with the analyzer 106 or the control system 104 of the system 100 or 100A, such that a system 100B is formed by the system 100 (or 100A) and the system 108.

It should also be noted that in some embodiments, the system 100 or 100A described above, can be configured and operable to generate recommendation data for intervention, e.g. by the analyzer 106, and to forward the recommendation data to an external plant growth control system communicating therewith, or to a work station (not shown) enabling a user to observe the recommendation data and decide about a suitable intervention.

The plant growth control system includes one or more plant growth modules 108M1-108MN, each configured to receive a respective recommendation data 108R generated by the analyzer 106, to thereby selectively apply one or more specific treatments to the plant(s). Generally, the term recommendation data 108R represents any portion of a recommendation data directed to any one of the plant growth modules described further below. After or while applying treatment to the plant(s), the one or more plant growth modules can optionally send feedback data 108F to the control system. The feedback data 108F can be processed, at the analyzer, in addition to the characterization data in order to determine about the need for further treatments. In some cases, the control system 104 may activate a first or second type data collection module to inspect the results of the applied treatment, immediately thereafter, and provide corresponding feedback data. Generally, the characterization data provided by the data collection modules, after a treatment has been performed to a specific location in the plant growing area, is sufficient for further decision making about the need of additional treatments.

In some embodiments, particularly when forming an integral part of the system 100 (or 100A), the plant growth modules can be carried by one or more unmanned vehicles that bring the plant growth modules near the specific plant(s) to be treated as identified in the recommendation data 108R, in a way similar to the data collection modules/devices of the data collection system 102. The vehicles are controlled by the control system 104 (whether it is distributed or centralized), or by a local control system (not shown) included in the plant growth control system 108, such that the plant growth control system 108 is operated automatically and autonomously.

The plant growth modules include one or more of the following: a sprayer for delivering insecticide or other treatment, a beneficial biological agent(s) distributor, a leaf and branch pruning module, a fruit thinning module, a fruit picking module, a humidifier for adjusting humidity conditions, an air conditioner for adjusting temperature in the plant(s) surrounding, a light source and shading mechanism for adjusting lighting conditions required for the growth of the plants.

The analyzer 106 analyzes the received characterization data, be it for example the characterization data 102C1 from the first data collection module 102M1 and/or the characterization data 102C2 from the second data collection module 102M2 and/or characterization data 102C3 in the form of environmental data from the third data collection module 102M3 and/or characterization data 102CN from another data collection module 102MN and possibly also data from an external source, such as a weather forecast, or any combination thereof. Upon determining that certain conditions are met, such as existence or condition of pest insects, beneficial insects, fungi, insect generated liquid drops, insect webs, and diseases, the analyzer generates the respective recommendation data to the suitable plant growth module. Furthermore, the analyzer may generate prediction data of expected evolution of the existing conditions based on the characterization data, environmental data and weather forecast and may generate proactive recommendation data to the suitable plant growth module.

The recommendation data 106R may be indicative of one or more of the following: treatment data indicative of a plant treatment plan, and environmental data indicative of an environmental condition change in the plant growing area. The plant treatment data may be generated for the whole plant growth area or locally for a part of the growth area, and can be indicative of one or more of the following: insecticide spraying, beneficial insect spreading, irrigation planning, fertilization planning, fruit picking or thinning, leaf and branch pruning, plant trellising, temperature change, humidity change, lighting change.

The analysis of the characterization data may include analysis of presence of multiple types of pest insects and the corresponding beneficial insects used to treat the pests, and analysis of the local ratio of beneficials to pests as well as a global aggregate score. The score may include a correlation of the density of the beneficials to density of the pests to determine the efficiency of previous treatment. For example, if the overall aggregate level of beneficials to pests is low, a general distribution of beneficials will be recommended. If the overall amount of beneficials in the cultivated area is sufficient, but the local ratio of beneficials to pests is low in specific areas, the analysis may indicate a compensating treatment to increase the beneficial density in areas where the ratio is low. A map can be generated with the required type of treatment and beneficial density per area.

Figure 6:
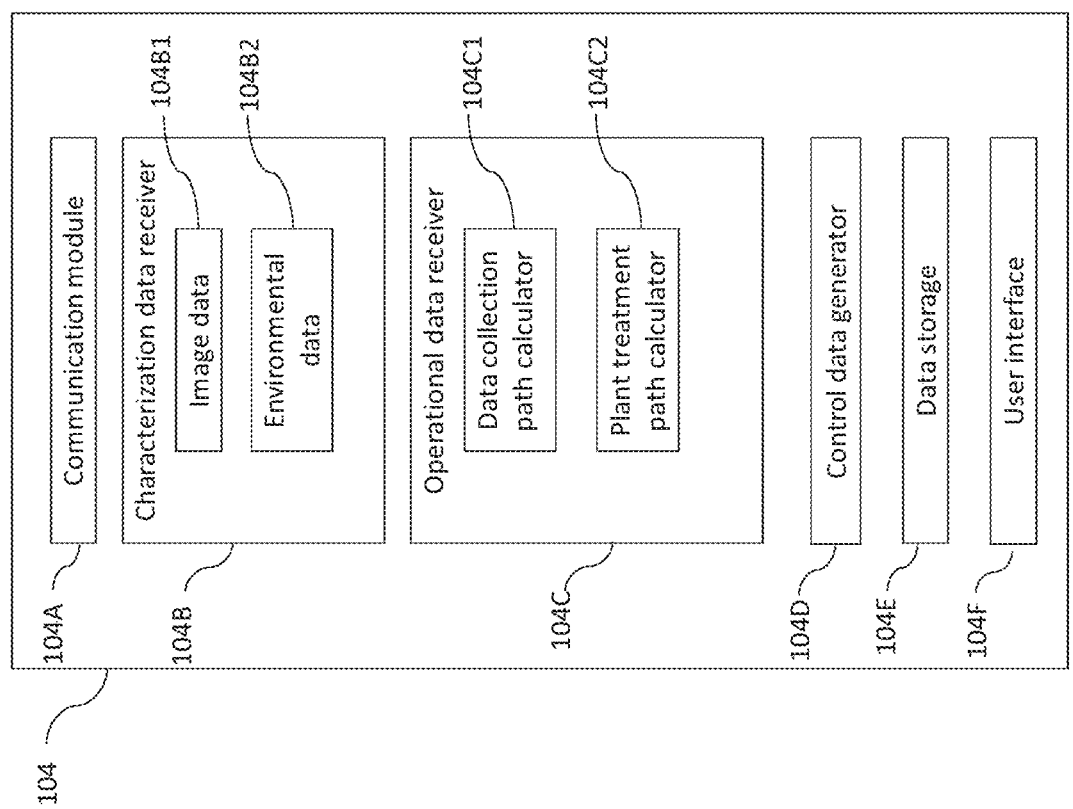
FIG. 6 illustrates, by way of a block diagram, a non-limiting exemplary embodiment of a control system configured and operable to control the data collection system and/or the plant growth control system, in accordance with the present invention.

Reference is made to FIG. 6 illustrating, by way of a block diagram, a non-limiting exemplary embodiment of a control system 104 configured and operable to be responsive to operational data received from the analyzer and to control the data collection system and/or the plant growth control system, in accordance with the present invention. In the figure, various functional modules of the control system are illustrated.

The control system is generally a computer system having data input and output utilities, memory and data processing utility, and is configured to be in data communication with the data collection system and the analyzer and with the plant growth control system whenever provided, through one or more communication modules 104A exploiting communication techniques and protocols known in the art. The control system can be configured as a local station communicating with a local data collection system and/or a local plant growth control system in the plant growing area (e.g. a single greenhouse), or as a central station communicating with one or more local data collection systems and/or one or more local plant growth control systems located respectively in one or more plant growing areas. The control system is configured to activate one or more data collection modules/devices either separately or collectively, sequentially or simultaneously.

A characterization data receiver module 104B is configured to continuously receive characterization data received from the one or more data collection modules of the data collection system, this includes image data 104B1 collected by the first and second type imaging devices, environmental data collected by sensors of the environmental sensing module and other sensor readings of plants. In addition, the characterization data received includes time, location and/or angular direction data indicative of real time action, time, angular direction and location of each data collection module and/or device. In some embodiments, the characterization data receiver module is configured and operable to partially process the characterization data before sending it to the analyzer. The characterization data receiver module can be configured to receive feedback data from the plant growth modules, or a separate receiver module can be included in the control system.

An operational data receiver module 104C is configured to receive the operational data from the analyzer. The operational data are generated by the analyzer based on the analysis of the characterization data. The operational data receiver can include data collection path calculator 104C1 configured and operable to calculate the path(s) for one or more data collection modules to perform targeted imaging and/or measurements from part(s) or all of the plant growing area(s) covered, and a plant treatment path calculator 104C2 configured and operable to calculate the path(s) for one or more plant growth modules/devices to apply targeted treatment to part(s) or all of the plant growing area(s) covered. It is noted that the path calculation may alternatively be performed at the analyzer, or at least partially performed at the analyzer, where the control system generates and allocates the specific paths for the specific data collection modules and/or the plant growth modules. For example, the analyzer provides a map of areas requiring a specific treatment and the control system calculates the optimal allocation of plant growth modules and their optimal path of travel.

A control data generator 104D provides, through the communication module 104A, the operational data to the data collection modules and/or the plant growth modules.

The control system may also include a memory (data storage utility) 104E configured and operable to temporarily or permanently save history of the characterization data, the operational data, the navigation data, the recommendation data and/or the feedback data. Possibly, the data storage utility can save data relating to the local plant growing area covered by the local control system.

The control system can also include a user interface module 104F configured and operable to report to a user at least one or more of the following: collected characterization data, analysis of characterization data, recommended treatment plans data, feedback data from the plant growth control system, planned path(s) for data collection and/or treatment plan(s). The user interface module can also be configured and operable to enable the user to modify and/or adjust the recommended treatment plans data, planned path(s) for data collection and/or treatment plan(s).

Figure 7:
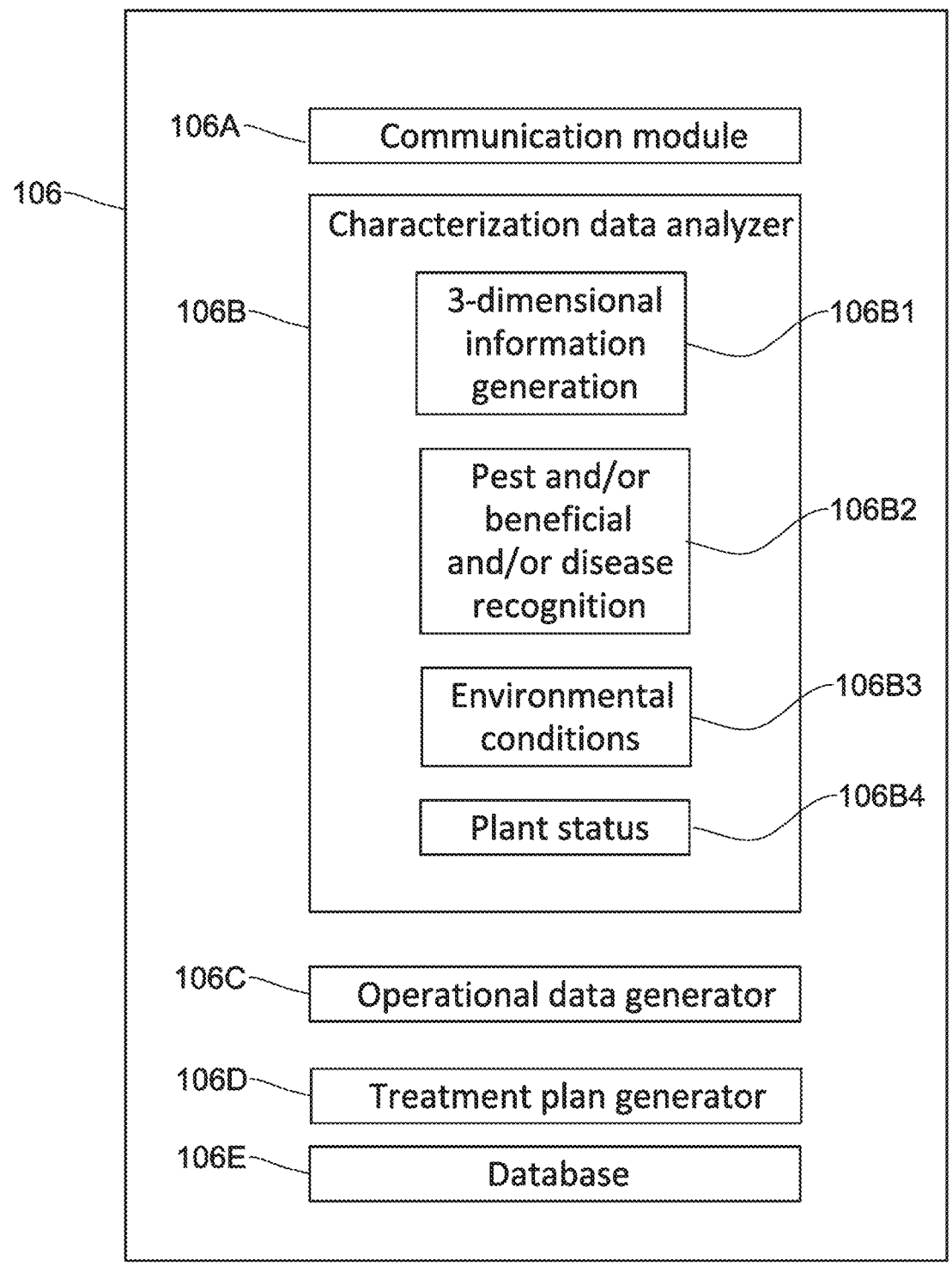
FIG. 7 illustrates, by way of a block diagram, a non-limiting exemplary embodiment of the analyzer being configured and operable to receive and analyze characterization data collected by the data collection system, and to generate the operational data and/or the recommendation data to control the data collection system and/or the plant growth control system respectively, in accordance with the present invention.

Reference is made to FIG. 7 illustrating, by way of a block diagram, a non-limiting exemplary embodiment of the analyzer 106 configured and operable to receive and analyze the characterization data collected by the data collection system, to generate the operational data and/or the recommendation data to control the data collection system and/or the plant growth control system respectively, in accordance with the present invention. In the figure, various functional modules of the analyzer are illustrated.

The analyzer 106 is generally a data processing utility and includes functional modules configured and operable to analyse the characterization data and provide as an output the operational and recommendation data described above. The analyzer 106 includes a communication module 106A, a characterization data processor module 106B, operational data generator 106C, and a treatment plan generator 106D, and includes or is in data communication with a database 106E.

The communication module 106A is configured and operable to enable input/output communication with the rest of the system parts, according to known communication techniques. The characterization data processor and analyzer 106B is configured and operable to analyze the characterization data being collected. The analysis results include 3-dimensional plant information 106B1 deduced from the analysis of the characterization data obtained from images captured by the wide-area detection module(s); pest and/or beneficial and/or disease recognition 106B2 based on images and data collected by various modules, environmental conditions determination 106B3, and plant status description/recognition 106B4, where the plant status includes, for example, one or more of the following: relative growth status (e.g. slow growth), hydration condition (e.g. lack of water), plant shape (e.g. broken stem), and plant health. The analysis may be based on machine learning techniques as described above. It may be based on comparison with past analysis results, on comparison with accessible knowledge-base available on the internet such as images of plants and plants parts (flowers, fruit, etc.), and/or on user input. The pest and/or beneficial and/or disease recognition 106B2 and plant status description/recognition 106B4 may be analysed using information generated by the 3-dimensional plant information generation 106B1, as well as the received characterization data 102C.

Based on the analysis, the operational data and treatment plan generators, 106C and 106D, are configured and operable to generate operational data for the data collection system and recommendation data for the plant growth control system, to thereby apply data collection and/or plant treatment.

The analyzer includes or is configured and operable to access a database 106E to thereby save the analysis results in the database or retrieve past analysis results to be used in the analysis of the current data. The database can be part of the analyzer or an external utility accessible by the analyzer.

For example, the analyzer can compare data from first type imaging device to data stored in database from previous inspections and then generate operational data for second type of imaging device at locations where data comparison exhibits abnormal change.

The analyzer may process the characterization data and determine objects of interest and calculate coordinates of specific locations to be inspected or treated.

The operational data may include location coordinates and vector information for operation of second type imaging device at specific location.

The analyzer may analyze multiple overlapping images of a plant area and generate 3-dimensional plant shape data, including at least some of: leaves, branches, stalks, flowers and fruit. The images may preferably be wide-area images captured by the first type data collection modules.

The analyzer may analyze the 3-dimensional plant shape data, determine objects of interest and calculate location coordinates and/or unobstructed approach vectors to specific locations.

The operational data may include optimized path between specific locations for second type imaging device, or optimized path connecting multiple specific locations for second type imaging device.

The functionality of the system of the invention and the interaction between the different parts/utilities are further exemplified herein after in non-limiting examples.

The data collection system includes at least one vehicle carrying one or more data collection modules and at least one base station. The at least one vehicle performs inspection runs to inspect the plants in a predefined crop area, where a run includes an aerial or ground path between multiple rows of plants. The path may include all rows of the cultivated area or a subset of rows. During the inspection run, the system collects plant data including, but not limited to, images or other sensor readings of plants, selected images of leaves, flowers, and fruit, and images of the crown of the plants. In one example, a wide-area imaging device and a high-resolution imaging device may be provided and located on separate vehicles. The wide-area imaging device may capture images of diagonal dimensions of between 20 cm and 100 cm or between 100 cm and 500 cm. For example, at least one vehicle with a wide-area imaging device performs an inspection scan of the rows of crops and at least one vehicle with a high-resolution imaging device performs imaging of individual leaves, flowers and fruit. In another example, a vehicle with a wide-area imaging device travels ahead of at least one vehicle with a high-resolution imaging device with a predetermined delay in order to prevent simultaneous operation in the same part of a row. For example, if operating in a greenhouse, wherein the aisles between rows are blocked at one end, the high-resolution imaging device will be timed so as to enter the aisle only after the wide-area imaging device has completed the aisle scan and exited the aisle.

The paths of all the vehicles may be planned in advance. Alternatively, the data from the wide-area imaging device is analyzed and immediate recommendations are made for making changes to the path of the at least one high-resolution imaging device. If the results from the wide-area imaging device show misshapen leaves on a specific plant, at least one sampling point is added on the plant and the high-resolution imaging device is sent to perform high-resolution imaging of the top side and underside of the leaves on the specific plant to determine the presence of pests or whether a viral condition exists.

The base station provides communication, navigation, cleaning and replenishment services to each vehicle. The control system records the at least one vehicle's location during inspection runs. The analyzer analyzes the characterization data and recommends specific treatments to be carried out at different locations in the inspected area, based on pest and disease evolution stage and severity, expected weather conditions, and others.

The control system/analyzer determines a path for the at least one plant growth module, including location, height, width and dose of the treatment. The at least one plant growth module performs the distribution of beneficial biological agents and/or the spraying of insecticides at the specific locations as required. The plant growth modules may be associated with the same base-station as the data collection modules or may use a separate base-station.

The automated system 100 (100A) can be used at multiple crop sites in order to increase the utilization of the system, reduce the cost of ownership and increase profitability. When used at multiple sites growing similar types of crops, the management of the cycling of the system between sites can be done based on a repetitive cycle of adjustable or predetermined frequency. Based on economic and utilization calculations, the analyzer/control system may recommend increased frequency of runs, while changing the run protocol (e.g. reduced percent of rows sampled or reduced number of samples per row) in order to retain the same overall growing-sites cycle frequency. The analyzer/control system may vary the run protocol at a certain crop site, if a detrimental condition is encountered, while minimizing the impact to other sites in the cycle. In one example, this can be achieved by adding additional vehicles to be operated by the control system.

Multiple vehicles may be operated to work in parallel to decrease the total operating time of the system. In one example, multiple vehicles carrying multiple data collection modules may be operated in parallel and the control system/analyzer provides the vehicles with non-intersecting travel paths. In addition, the vehicles may communicate with each other to aid prevention of collisions. The control system/analyzer may utilize information provided by some of the data collection modules in order to optimize the paths of other data collection modules.

The plant monitoring and/or treatment system can be designed to be easily transported between crop sites, either as a towable wagon or on a towable wagon.

In one specific non-limiting embodiment, the automated system is operated in greenhouses. The wagon is wheeled into a greenhouse and placed at an optionally predetermined location. An operator/user uses a control panel, connected to the control system, and chooses an inspection plan. The at least one vehicle departs autonomously from the base station in a predetermined inspection plan. The vehicles return periodically, if needed, to charge or exchange their batteries. The inspection plan may include the timing for battery replenishment, taking into account the specific payload of the vehicle and the weather conditions. If the vehicles are drones, the drones take off autonomously from their landing pads in a predetermined inspection plan. The drones return periodically, if needed, to charge or exchange their batteries. The inspection plan may include the timing for battery replenishment, taking into account the specific payload of the drones and the weather conditions.

Inspection runs (imaging sessions) are performed periodically and the results are compared from run to run. The inspection runs may include data collection from a combination of at least some of: wide-area imaging device, high-resolution imaging device, infra-red imaging device, environmental sensors located in the crop area (e.g. including temperature sensors, humidity sensors). If required, the analyzer may immediately, during or following a run, recommend that the vehicle return to a specific location and perform additional data collection. This may occur, for example, when a detrimental effect is seen in the morphology of leaves in a specific area, as sampled by a wide-area imaging device, and the analyzer determines that high resolution samples should be carried out on leaves in the specific area, or if the sampled data from the location is found to be insufficient as in the case of a low area success parameter.

The inspection plan used in an inspection run is determined by the control system/analyzer, based on a number of factors including stage of plant growth, inspection history of the specific crop area, treatment history of the crop area, weather, size of the crop area, system time availability, cost of operation and manual inputs from the user. Tradeoffs can be defined for the inspection rate (i.e. number of rows per hour) versus the sampling detail level (e.g. number of samples of leaves and flowers collected per row) depending on the above factors.

Inspection runs are carried out at a frequency determined by the typical rate of development of pest infestations and disease development, typically once per week. Depending on the season and environmental conditions such as temperature and humidity, run frequency adjustment can be recommended by the analyzer/control system. The analyzer/control system may also recommend adding a run or varying the protocol of a run to increase the sampling density of a certain area of the growing site in order to verify the effectivity of a specific treatment action previously carried out.

The analyzer communicates with the control system and/or directly with a vehicle, receives the data and performs analysis, to generate information on the status of the plants and location and severity of detrimental conditions. The analyzer provides operational data in the form of tabular data, density maps of parametric data, maps with embedded data such as photographs, recommended treatment maps such as beneficial type and distribution density and insecticide type and spraying parameters, irrigation parameters, fertilizer parameters and others. The analysis data and data of the collection runs can be saved in the database.

Figure 8:
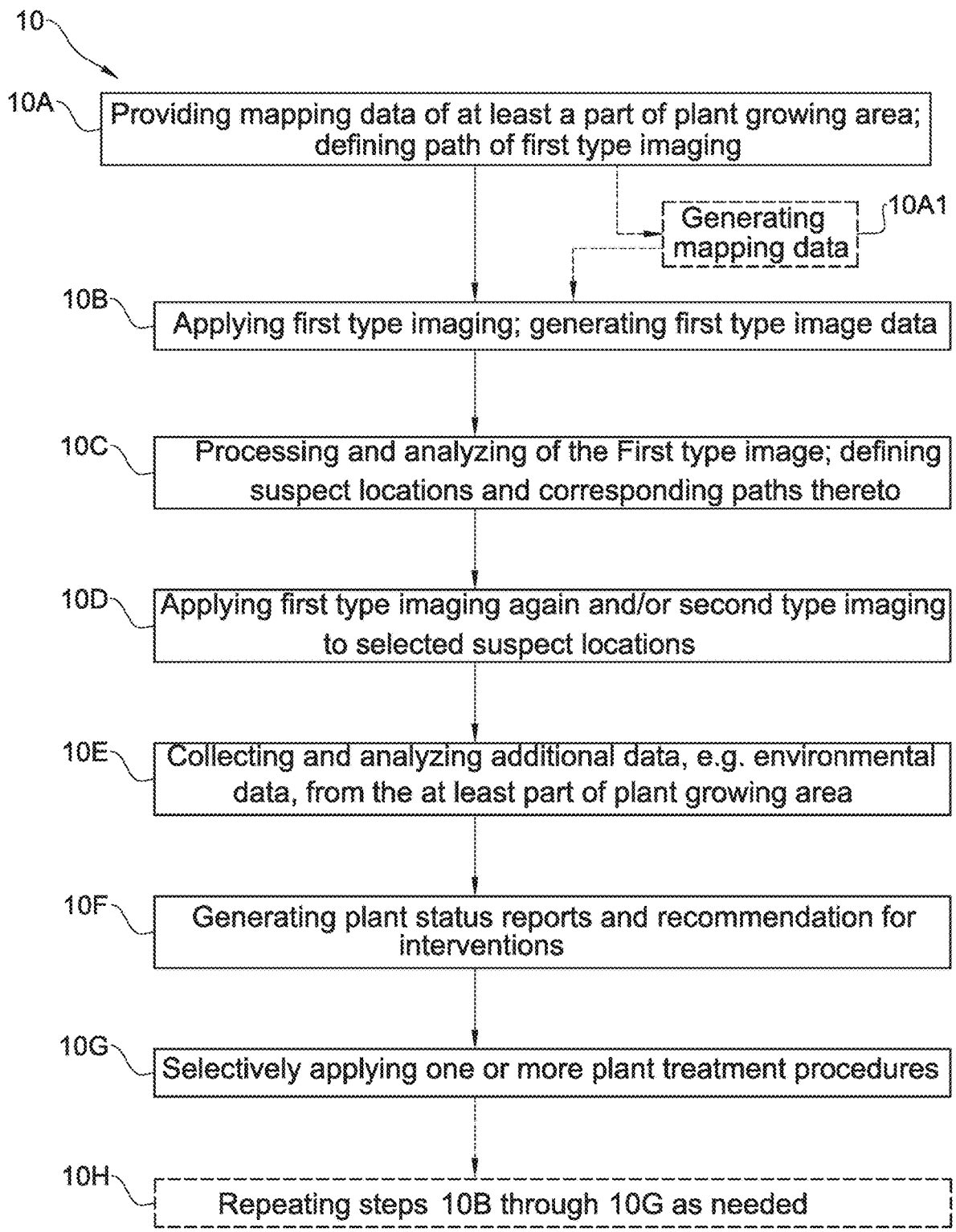
FIG. 8 exemplifies a method of the invention for monitoring and/or treating plants in a plant growing area.

Reference is made to FIG. 8 illustrating a non-limiting exemplary of a flow diagram 10 of a method for monitoring and/or treating plants in a plant growing area, according to the invention. The method can be executed, for example, by any of the systems described above.

At step 10A, mapping data of at least part of the plant growing area is provided and data collection path of a first type imaging is defined. In one example, at 10A1, if mapping data is not available, a mapping run is applied to the at least part of the plant growing area (for example, to the whole plant growing area monitored), and a mapping data of the at least part of the plant growing area is generated and saved for use in future runs.

At step 10B, the first type imaging is applied to at least a part of the plant growing area while moving along the at least part of the plant growing area, and a first type image data (first characterization data) indicative of various parameters of plants being imaged in the at least part of the plant growing area is generated. In one example, the first type imaging is a wide-area imaging characterized by a wide field of view and low, but sufficient, resolution. If mapping data is not available, the first run of the first type imaging is applied to the at least part of the plant growing area concurrently with collecting mapping data which is saved for use in future runs.

At step 10C, the first type image data is processed and analyzed. Locations including plants or parts of plants in the at least part of the plant growing area may be defined as suspect locations and at least one path to the suspect locations can be defined. As described above, the suspect locations can indicate one or more plant parameters such as diseases, pest presence, need for pruning, need for change in environmental conditions, etc.

At step 10D, if suspect locations and corresponding path(s) were defined, one or more of the following can be performed sequentially, partly simultaneously, or fully simultaneously: the first type imaging may be applied again to one or more selective suspect locations; a second type imaging is applied to one or more selective suspect locations. The second type imaging is characterized by a narrower field of view and a higher resolution than the first type imaging.

In one example, steps 10B and 10D (concerning the second type imaging) can be applied partly simultaneously, with a time delay, or fully simultaneously with a path difference, between the first and second type imaging types, such that the first type imaging is applied and analyzed, and a path for the second type imaging is continuously adjusted/redefined (augmented) while the first type imaging is running.

At step 10E, further data collection from the at least part of the plant growing area can be applied and the data is analyzed. For example, environmental data of one or more types can be collected, e.g. light conditions, temperature, humidity, etc. The analysis of the collected environmental data can be used to update the suspect locations and accordingly the paths of the ongoing or next runs of the first, second and/or environmental data types.

At step 10F, the analysis produces reports of the status of the plants in the plant growing area and possible recommendations for plant treatment. The reports may be in the form of density maps, tabular data and/or additional formats. The recommendations may be regarding plant treatments, procedures, environmental conditions and others. In some embodiments, a user may review the recommendations and perform adjustments.

At step 10G, one or more plant treatment procedures, such as application of insecticide, delivery of beneficial insects or change in environmental conditions, can be applied to select locations in the at least part of the plant growing area, based on the analysis of the first type imaging, second type imaging or environmental data. The environmental data can include collected data or data fed from external sources such as weather forecasts. The data forming a basis for the analysis can be data collected over at least one run in the past.

At step 10H, optional targeted steps 10B to 10E can be applied, on a regular basis or by demand or based on previous analysis, after the application of a treatment procedure to estimate the treatment efficacy and recommend about further needed treatment(s).

Figure 9A:
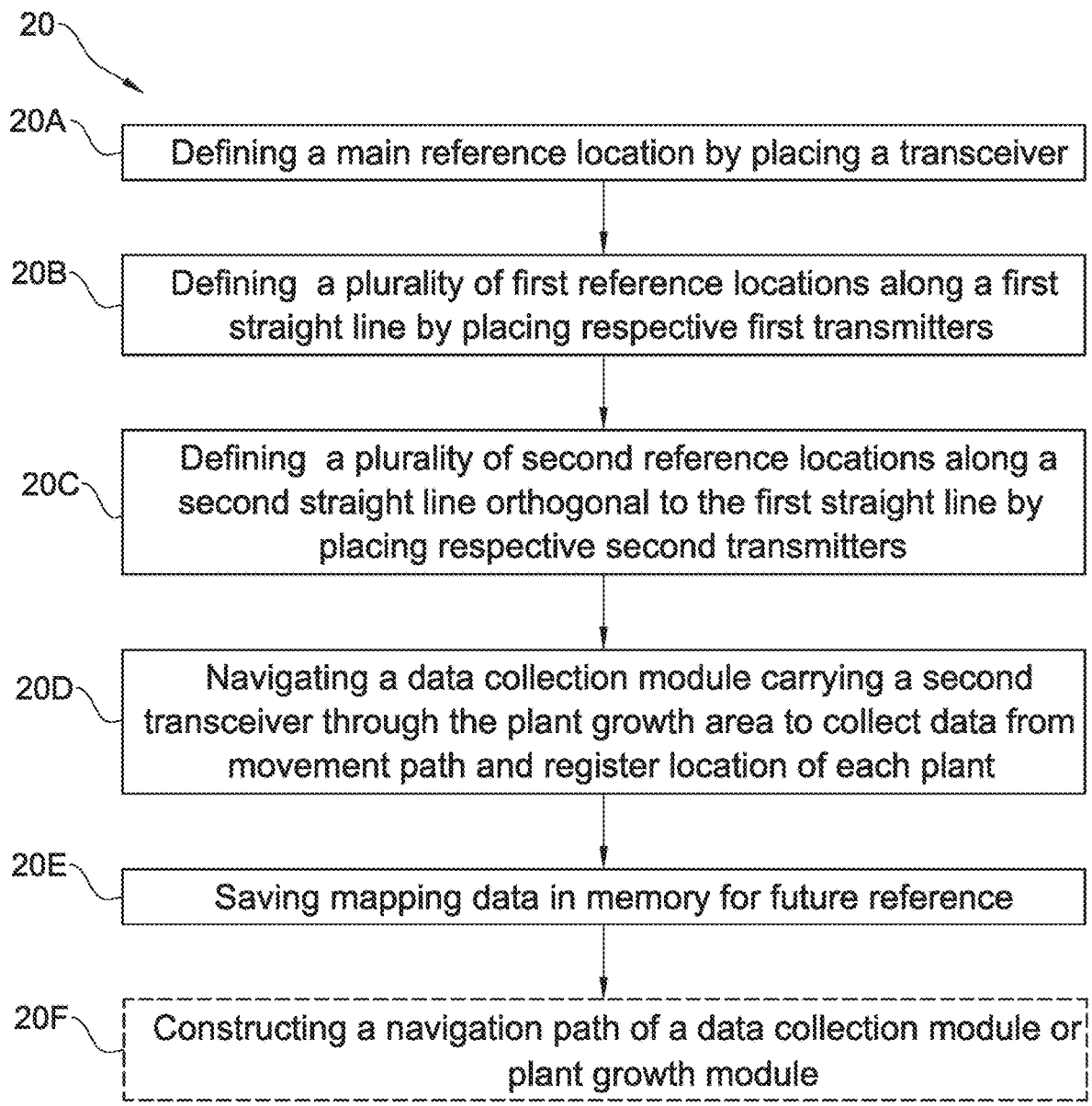
FIGS. 9A-9B exemplify methods of the invention for building mapping data and navigation in a plant growth area.
Figure 9B:
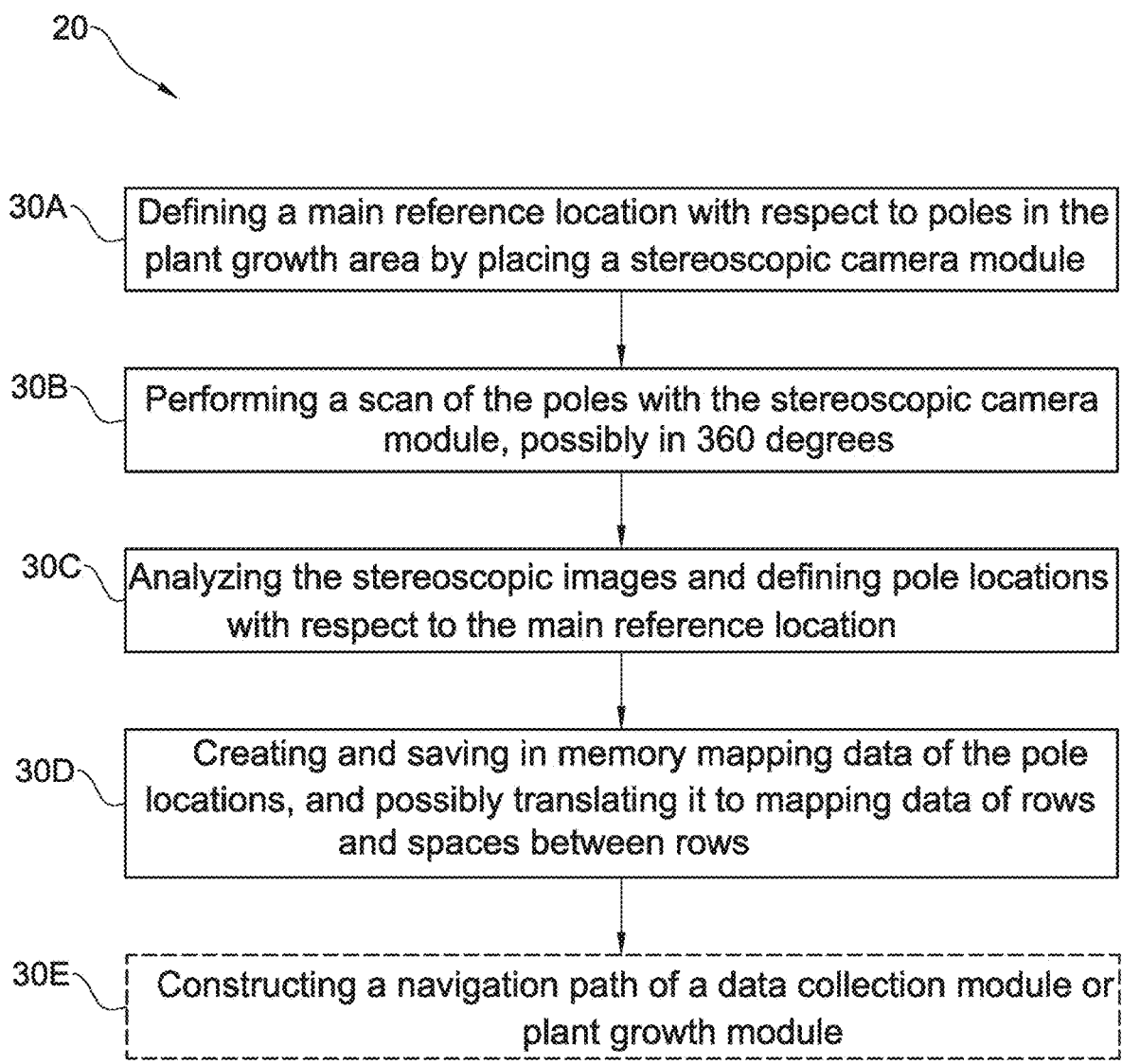

Reference is made to FIGS. 9A-9B, illustrating methods of building mapping data and navigation in a plant growth area, according to exemplary non-limiting embodiments of the present invention.

Navigation of the data collection modules and/or plant growth modules in the plant growth area utilizes mapping data that is either previously or concurrently built. Acquisition of the mapping data can be, among others, in one of two ways described herein below.

According to a first non-limiting example of a flow diagram 20 of a method, exemplified in FIG. 9A, the mapping data is obtained by utilizing triangulation methods by defining a plurality of reference locations throughout the plant growth area and defining any other location in the plant growth area in relation to the reference locations.

At step 20A, a main reference location is defined in the plant growth area. This can be done, for example, by placing a transceiver at the main reference location. The main reference location can be any location near the plant growth area. In one example, the main reference location is chosen to be the location of the local/central station in the plant growth area.

At step 20B, a plurality of first reference locations along a first straight line in the plant growth area are defined, for example by placing a respective plurality of first transmitters that communicate with the transceiver at the main reference location and define the relative location of each first reference location with respect to the main reference location.

At step 20C, a plurality of second reference locations along a second straight line, in the plant growth area, that is orthogonal to the first straight line are defined, for example by placing a respective plurality of second transmitters that communicate with the transceiver at the main reference location and define the relative location of each second reference location with respect to the main reference location and/or with respect to the first reference locations.

At step 20D, a data collection module carrying a second transceiver communicating with the transceiver at the main reference location and receiving signals from the transmitters, can be brought to navigate the plant growth area to collect data in the row including movement path and plants position and register location of each plant using triangulation.

At step 20E, mapping data of movement paths and all plants in the plant growth area is acquired and can be saved in memory/database for future reference.

At step 20F, a navigation path of the data collection and/or plant growth module can be constructed based on the mapping data and the data collection and/or plant growth module, carrying a third transceiver communicating with the transceiver at the main reference location and at least two transmitters, can be brought anywhere to any plant in the plant growth area.

In FIG. 9B, a flow diagram 30 of a second non-limiting example of a method for building the mapping data is shown. It is prevalent that in plant growth areas, such as a greenhouse, plant supporting poles and/or structural poles are positioned within the plant growth area. It is possible to map the locations of the poles and use their locations as reference data for building a navigation path for the data collection and/or plant growth modules.

This can be performed by at least two cameras operating in stereoscopic mode. At step 30A, a main reference point is defined within the plant growth area by placing there a stereoscopic camera module. The scan can also be performed with a single camera placed sequentially at multiple predetermined locations.

At step 30B, a scan is performed in a horizontal plane using the stereoscopic camera module. The scan can be in 360 degrees, and performed at a height above that of the plants in order to provide a clear field of view of the plant supporting poles and/or structural poles. Improved accuracy can be achieved by scanning from additional locations within the growth area.

At step 30C, the stereoscopic images are analyzed and pole locations are defined, e.g. by calculating distances and angles between each pole location and the main reference location.

In cases where ambiguity arises in pole location, additional scans can be performed at different locations within the plant growth area.

At step 30D, mapping data of the location of plant supporting poles and/or structural poles can be created and saved in a memory for future reference. The map of pole location can be transformed into a map of planted rows and spaces between rows.

At step 30E, navigation path of a data collection and/or plant growth module can be constructed. The data collection and/or plant growth module carrying a camera module can be programmed to navigate in a path along the spaces between rows autonomously, by analyzing images it captures while navigating with the mapping reference data. Optionally, the data collection and/or plant growth module can perform a path verification, e.g. at the entrance to each aisle between rows, by capturing a stereoscopic image of the supporting structure of the specific row and comparing the image to the saved mapping data. The data collection and/or plant growth module can continuously monitor its location along its path by monitoring the poles on one or both sides, in front and behind, by imaging with the camera module, possibly a non-stereoscopic camera.

The data collection and/or plant growth module can maintain its position at the center of the aisle between rows by monitoring the distance to the poles on either side by one or more stereoscopic cameras. In cases where a path is required to be closer to a row of plants on one side of the space, the path can be controlled by a camera which maintains a determined distance from the plant. Other sensors can also be used including acoustic and laser sensors.

The map of planted rows and aisles is utilized as a base and reference for the data collected by the data collection and/or plant growth module.

The pole mapping data can be used in conjunction with a transmission based system such as, but not limited to, Wi-Fi, Bluetooth, ultra-wide-band, radar, acoustic transmitters, where the pole mapping data can be used for guidance for determining the navigation path and the transmission based system is used to electronically record the coordinates of the data collection and/or plant growth module throughout the path and especially during recording of data points with significant findings.

The height of the findings can be determined by the images from the data collection and/or plant growth module, by the transmission-based system using, for example, triangulation, or by various sensors located on the vehicle such as acoustic sonar sensors (transducers), infra-red, laser or others.

As can be well understood, the present invention thus provides a comprehensive technique for automatic quality monitoring and treatment of plants, thereby increasing the plant growing efficiency.

The invention claimed is:

1. A monitoring system for monitoring plants' conditions in one or more plant growing areas, the system comprising:
   a data collection system configured and operable to provide characterization data about plants in said one or more plant growing areas, the data collection system comprising data collection modules of at least first and second different types, wherein the first type data collection module comprises a first imaging device of predetermined first field of view and first resolution and the second type data collection module comprising a second imaging device of predetermined second field of view and second resolution being, respectively, narrower and higher than the first field of view and the first resolution, the characterization data comprising first image data provided by the first imaging device being indicative of various parameters of the plants being imaged by said first imaging device;

a control system configured and operable to selectively activate the second type imaging device to apply the second type imaging to at least a part of said one or more plants, based on operational data obtained from the characterization data derived from said first image data provided by the first imaging device, the control system having either one of the following configurations:

the control system is configured and operable to be in data communication with an analyzer located at a central station and is responsive to the operational data received from the analyzer and selectively activate the second type imaging device to apply the second type imaging to at least a part of said one or more plants; and the control system comprises an analyzer configured and operable for analyzing the first image data provided by the first imaging device and generating said operational data to selectively activate the second type imaging device to apply the second type imaging to at least a part of said one or more plants.

2. The system according to claim 1, wherein the first imaging device is configured and operable to acquire multiple overlapping images during an image acquisition session while travelling along a first movement path extending substantially parallel to a row along which plants are arranged in a spaced-apart fashion and performing relative movement with respect to each plant being imaged, with an optical axis of the first imaging device being a horizontal axis oriented substantially perpendicularly to said first movement path, said first image data being therefore indicative of said multiple overlapping images, the operational data obtained from the first image data provided during the image acquisition session of the first imaging device comprises navigation data for a second movement path of the second imaging device towards one or more selected plants from a position and direction enabling an unencumbered approach for capturing images of suspect locations of said one or more selected plants while enabling to minimize physical interaction with said one or more selected plants.

3. The system according to claim 1, wherein the control system is further configured and operable to perform one or more of the following:

activate imaging sessions of the first and second type imaging devices to be performed at least partially simultaneously;

selectively adjust a movement path of the second type imaging device during an imaging session of the second type imaging device, based on the image data obtained by the first type imaging device prior to or during said imaging session performed by the second type imaging device;

control movement of the second type imaging device along foliage at a predetermined distance enabling imaging of the plants, and upon identifying a potential suspect location from the first image data, operating said second type imaging device to approach the suspect location and perform imaging thereof; and determine at least one movement path for at least one of said first or second type imaging devices to access one or more suspect location.

4. The system according to claim 1, wherein said data collection modules are configured and operable to be in data communication with the analyzer, for communicating the characterization data to said analyzer, thereby enabling generation of output data indicative of plant status for each plant being imaged based on analysis of said characterization data, said output data comprising data indicative of a predetermined condition of said one or more plants being imaged by at least one of the first type and second type imaging devices, the control system further providing recommendation data to a plant growth control system.

5. The system according to claim 1, wherein the control system comprises the analyzer configured and operable to carry out one or more of the following:

analyze first type image data obtained in an imaging session performed by the first type imaging device by comparing said first type image data to pre-stored image data obtained in one or more preceding imaging sessions by at least one of the first and second type imaging devices;

analyze at least one of the first type image data and second type image data obtained by, respectively, at least one of the first type imaging device and second type imaging device, and determine one or more suspect locations within the at least part of the plant growing area; and utilize input data about geometrical dimensions and degrees-of-freedom of motion of the second type imaging device to analyze the first image data to determine a three-dimensional model of the plant being imaged and extract accessible volumes which can be utilized by the second type imaging device to perform imaging.

6. The system according to claim 1, characterized by one or more of the following:

the system is configured and operable to utilize the image data obtained by at least one of the second type imaging devices to optimize analysis of the image data provided by at least one of the first type imaging devices;

the system is configured and operable to analyze image data provided by the first type imaging device being indicative of multiple overlapping images collected during an image acquisition session while travelling along a movement path in the plant growing area and generate three-dimensional plant shape data associated with said plant growing area and including at least some of: leaves, branches, stalks, flowers and fruit of the plants in said plant growing area;

the system is configured and operable to analyze image data provided by the first type imaging device being indicative of multiple overlapping images collected during an image acquisition session while travelling along a movement path in the plant growing area and generate three-dimensional plant shape data associated with said plant growing area, said three-dimensional data combined with color information of leaves, enabling separation of variation caused by lighting from variations caused by leaf discoloration.

7. The system according to claim 1, configured and operable to analyze image data indicative of multiple overlapping images obtained by of the first type imaging device during an image acquisition session while travelling along a movement path in the plant growing area and generate three-dimensional plant shape data associated with said plant growing area and including at least some of: leaves, branches, stalks, flowers and fruit of the plants in said plant growing area, the system being characterized by one or more of the following:

said multiple overlapping images comprise at least one in-focus image and at least one out-of-focus image obtained by said at least one of the first imaging device and second imaging device, enabling to determine three-dimensional outline of the plant or parts thereof from at least two images including the at least one out-of-focus image, and determine details of surfaces from the at least one in-focus image; and the system is further configured and operable to analyze said three-dimensional plant shape data and determine one or more suspect locations in the plant growing area.

8. The system according to claim 1, comprising one or more vehicles carrying the data collection modules, said one or more vehicles comprising one or more of unmanned aerial vehicle and unmanned ground vehicle, and being characterized by one or more of the following:

at least one vehicle from the one or more vehicles carries at least one of the first type and second type collection modules;

the first type and second type collection modules are carried by first and second vehicles, respectively.

9. The system according to claim 1, characterized by one or more of the following:

the operational data further comprises one or more of the following: tabular data, density maps of parametric data, maps with embedded data, recommended treatment maps the data collection system further comprises one or more sensors configured and operable to monitor one or more environmental conditions of the plant growing area, and provide environmental data indicative of said one or more conditions; the characterization data provided by either one or both of the first and second type imaging devices comprise data indicative of one or more the following: whole plant images, leaf images, leaf underside images, flower images, plant crown images, fruit images, branch images, images of supporting wires and poles;

each of the first and second types imaging devices is configured and operable to perform imaging using one or more of the following illumination schemes: visual spectrum, IR spectrum, IR, multi-spectral imaging, exciting illumination causing fluorescence response of plants being imaged, exciting illumination causing fluorescence response of insects being imaged.

10. The system according to claim 9, wherein the characterization data provided by the data collection modules further comprises one or more of the following: temperature parameters, air humidity parameters, wind direction and speed parameters, weather forecast, soil humidity parameters, sunlight parameters, soil nutrient parameters.

11. The system according to claim 1, wherein the control system comprises the analyzer configured and operable to analyze the first image data and generate said operational data to selectively activate the second type imaging device to apply the second type imaging to at least a part of said one or more plants, the analyzer being adapted to carry out the following:

process the characterization data provided by one or more of the first type imaging device and second type imaging device and three-dimensional plant shape data associated with said plant growing area and determine one or more of the following plant characteristics: plant structure, plant height, plant biomass, leaf color, leaf outline including one or more of leaf size, leaf angle, leaf shape and leaf distortion, fruit size, fruit location and height from the ground, fruit orientation, fruit shape, fruit color and fruit ripeness, flower location and height from the ground, flower orientation, leaf discoloring, pest insects, beneficial insects, fungi, insect generated liquid drops, insect webs, and diseases; and analyze said one or more determined plant characteristics in accordance with the one or more predetermined conditions to selectively generate recommendation data to a plant growth control system, said recommendation data comprising one or more of the following: (i) treatment data indicative of a plant treatment plan including one or more of the following: insecticide spraying, beneficial insect spreading, irrigation planning, fertilization planning, fruit picking, fruit thinning, leaf and branch pruning, plant trellising; and (ii) environmental data indicative of an environmental condition change in the plant growing area.

12. The system according to claim 1, wherein said control system is configured and operable to utilize the parameters of the plants determined from one or more of the first and second type image data to provide output data indicative of at least a part of the plant growing area, the output data including data indicative of one or more of the following: plant height compared to plant age/growth cycle, plant height distribution, plant biomass, leaf size, color and density distribution, fruit size, ripeness, color, density and height distribution, flower density and height distribution, branch quantity, density and height distribution, specific pest insects density, specific beneficial insects density, ratio of specific beneficial insects to specific pest insects, fungi density, and diseases density.

13. The system according to claim 11, wherein said recommendation data, is indicative of one or more operations to be performed by one or more plant growth modules providing one or more of: insecticide spraying, beneficial spreading, irrigation planning, fertilization planning, fruit picking, fruit pruning, leaf and branch pruning.

14. The system according to claim 11, wherein said recommendation data comprises treatment data indicative of a plant treatment plan, the treatment data being in the form of treatment maps that include at least some of the parameters: beneficial insect type, locations and density for spreading and insecticide type, locations and spraying parameters.

15. The system according to claim 2, characterized by one or more of the following:

said first type imaging device is configured to carry out one or more of the following: perform said imaging session while moving along said movement path substantially parallel to the row of plants; perform said imaging session while moving along said movement path substantially parallel to the row of plants with a varying height above ground; perform imaging of spaced-apart parallel rows of plants located on both sides of an aisle while moving along said movement path substantially parallel to the row of plants; and acquire the multiple overlapping images with periodically varying vertical locations with respect to the row of plants to thereby perform a sampling pattern of the row of plants;

said data collection system is configured such that at least two of the first type imaging devices are mounted in a spaced-apart relationship on a vertical support being therefore arranged at different heights, the system comprising a height adjustment mechanism configured and operable for adjusting vertical locations of the first type imaging devices in order to maintain a required overlap between the multiple overlapping images.

16. The system according to claim 2, wherein the first type data collection module comprises a flash illuminator configured and operable to provide one or more of pulse time and intensity of flash illumination selected in accordance with one or more of a velocity of said relative movement of the first type imaging device and a distance between the first type imaging device and the plant being imaged.

17. The system according to claim 2, characterized by one or more of the following:
at least one of the first type data collection module and the control system is configured and operable to periodically vary a velocity of the relative movement such that the velocity drops down to below a certain value when an image capture is required;
the first type data collection module comprises an angular motion mechanism, which is associated with at least one first type imaging device and is configured and operable to controllably rotate the optical axis of said at least one first type imaging device such that the optical axis is perpendicular to the plant being imaged during an image capture and velocity of angular rotation of the optical axis compensates for the movement of said at least one first type imaging device;
the first type data collection module comprises an angular motion mechanism associated with a pair of the first type imaging devices carried by said first type data collection module and being accommodated such that their optical axes are parallel, the angular motion mechanism comprising a controllable oscillator configured and operable to perform controllable oscillation of said optical axes in an alternating fashion such that oscillation velocity compensates for the movement of each of the first type imaging devices while maintaining the optical axes perpendicular to the row of plants during an image capture.

18. A monitoring system for monitoring plants' conditions in one or more plant growing areas, the system comprising:
a data collection system configured and operable to provide characterization data about plants in said one or more plant growing areas, the data collection system comprising data collection modules of at least first and second different types, the first type data collection module comprising a first imaging device of predetermined first optical properties and the second type data collection module comprising a second imaging device of predetermined second optical properties different from the first optical properties, the characterization data provided by at least one of the first and second imaging devices being indicative of various parameters of the plants being imaged;
a control system configured and operable to selectively activate the second type imaging device to apply the second type imaging to at least a part of said one or more plants, based on operational data obtained from the characterization data derived from first image data provided by the first imaging device, the control system having either one of the following configurations:
the control system is configured and operable to be in data communication with an analyzer located at a central station and is responsive to the operational data received from the analyzer and selectively activate the second type imaging device to apply the second type imaging to at least a part of said one or more plants; and
the control system comprises an analyzer configured and operable for analyzing the first image data provided by the first imaging device and generating said operational data to selectively activate the second type imaging device to apply the second type imaging to at least a part of said one or more plants;
wherein the first and second optical properties comprise, respectively first and second fields of view and resolutions, the second field of view and second resolution being, respectively, narrower and higher than the first field of view and resolution;
wherein the first imaging device is configured and operable to acquire multiple overlapping images during an image acquisition session while travelling along a movement path extending substantially parallel to a row along which plants are arranged in a spaced-apart fashion and performing relative movement with respect to each plant being imaged, with an optical axis of the first imaging device being oriented substantially perpendicularly to said movement path, said first image data being therefore indicative of said multiple overlapping images,
wherein the operational data obtained from the first image data provided during the image acquisition session of the first imaging device comprising navigation data for a movement path of the second imaging device towards one or more selected plants from a position and direction enabling an unencumbered approach for capturing images of suspect locations of said one or more selected plants while enabling to minimize physical interaction with said one or more selected plants;
characterized by one or more of the following:
at least one of the first type data collection module and the control system is configured and operable to periodically vary a velocity of the relative movement such that the velocity drops down to below a certain value when an image capture is required;
the first type data collection module comprises an angular motion mechanism, which is associated with at least one first type imaging device and is configured and operable to controllably rotate the optical axis of said at least one first type imaging device such that the optical axis is perpendicular to the plant being imaged during an image capture and velocity of angular rotation of the optical axis compensates for the movement of said at least one first type imaging device;
the first type data collection module comprises an angular motion mechanism associated with a pair of the first type imaging devices carried by said first type data collection module and being accommodated such that their optical axes are parallel, the angular motion mechanism comprising a controllable oscillator configured and operable to perform controllable oscillation of said optical axes in an alternating fashion such that oscillation velocity compensates for the movement of each of the first type imaging devices while maintaining the optical axes perpendicular to the row of plants during an image capture;
wherein the first type data collection module comprises an angular motion mechanism associated with a pair of the first type imaging devices carried by said first type data collection module and being accommodated such that their optical axes are parallel, the angular motion mechanism comprising a controllable oscillator configured and operable to perform controllable oscillation of said optical axes in an alternating fashion such that oscillation velocity compensates for the movement of each of the first type imaging devices while maintaining the optical axes perpendicular to the row of plants during an image capture, the system being characterized by either one of the following:
- the pair of the first type imaging devices are accommodated such that their optical axes while being parallel pointing in opposite directions;
- the angular motion mechanism further comprises a pair of light directing elements in the optical axes of said pair of the first type imaging devices, respectively, to redirect optical paths defined by the optical axes to opposite pointing directions, wherein the controllable oscillator is associated with either the pair of the light directing elements or the pair of the first type imaging devices.

19. The system according to claim 2, wherein the first type imaging device is characterized by one or more of the following:
- comprises an imaging sensor and an angular motion mechanism associated with said imaging sensor for controlling oscillatory motion of said imaging sensor to compensate for the relative movement;
- comprises a video camera operable with a certain video frame rate, and said first type data collection module comprises a rotatable reflective optical element or angular motion means being configured and operable to rotate the camera at a frequency corresponding to the video frame rate.

20. The system according to claim 2, wherein said first type data collection module is carried by a drone and is configured and operable to perform imaging sessions for plants in the row while performing the relative movement with respect to the plant being imaged, the system comprising an angular motion mechanism for controlling angular motion of the optical axis of the first imaging device by intentionally controlled yaw of the drone.

21. The system according to claim 2, wherein said first type data collection module is carried by a drone and is configured and operable to perform imaging sessions for plants in the row while performing the relative movement with respect to the plant being imaged, the system comprising rotors attached to the drone to create intentional controlled yaw of the drone, where an axis of rotation of the rotors is in a horizontal plane essentially perpendicular to, and at a radius from, a central axis of rotation of the drone.

22. The system according to claim 1, wherein at least one of the first type and second type data collection modules comprises a flash illuminator, said flash illuminator being configured and operable to carry out one or more of the following:
- provide a variety of illumination intensities for multiple image acquisitions of a plant with different illumination intensities, thereby optimizing three-dimensional modeling of the plant;
- provide a variety of exposure levels for multiple image acquisitions of a plant differing in one or more of illumination intensity and exposure time;
- provide a variety of exposure levels for multiple image acquisitions of a plant, the data collection module being associated with an angular motion mechanism.

23. A method for managing operation of a plant growing area, the method comprising:
- providing first type image data comprising a sequence of multiple overlapping first type images of relatively wide field of view and relatively low resolution of at least one row of plants in the plant growing area, said sequence of the first type images being acquired by a first type imaging device while moving along a first movement path substantially parallel to said row, with an optical axis of the first type imaging device being a horizontal axis oriented substantially perpendicular to the first movement path said first type image data being indicative of characterization data of various parameters of plants being imaged in said at least one row of the plant growing area;
- analyzing said first type image data to identify one or more suspect locations within said at least one row of plants, and selectively generating operational data to initiate activation of a second type imaging of relatively narrow field of view and relatively high resolution to be applied to one or more selective regions within said at least one row of plants of the plant growing area.

24. The method according to claim 23, further comprising selectively generating the operational data to initiate one or more of the following: activation of plant treatment procedure with respect to at least some regions within said at least one row of plants; and affecting one or more environmental conditions within the plant growing area.

* * * * *